US008658602B2

(12) United States Patent
Scaria et al.

(10) Patent No.: US 8,658,602 B2
(45) Date of Patent: *Feb. 25, 2014

(54) MULTIMERIC CONSTRUCTS

(75) Inventors: Abraham Scaria, Framingham, MA (US); Peter Pechan, Brookline, MA (US); Samuel Wadsworth, Shrewsbury, MA (US)

(73) Assignee: GenzymeCorporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/019,432

(22) Filed: Feb. 2, 2011

(65) Prior Publication Data

US 2011/0268735 A1 Nov. 3, 2011

Related U.S. Application Data

(63) Continuation of application No. 11/716,794, filed on Mar. 12, 2007, now Pat. No. 7,928,072, which is a continuation of application No. PCT/US2005/032320, filed on Sep. 13, 2005.

(60) Provisional application No. 60/608,887, filed on Sep. 13, 2004, provisional application No. 60/658,209, filed on Mar. 4, 2005.

(51) Int. Cl.
| C12P 21/04 | (2006.01) |
| C12N 15/00 | (2006.01) |
| C12N 9/48 | (2006.01) |
| A61K 38/17 | (2006.01) |
| C07K 14/705 | (2006.01) |
| C07K 14/71 | (2006.01) |
| C07H 21/04 | (2006.01) |

(52) U.S. Cl.
USPC ...... 514/20.6; 435/69.7; 435/212; 435/320.1; 536/23.4; 514/1; 530/350

(58) Field of Classification Search
None
See application file for complete search history.

(56) References Cited

U.S. PATENT DOCUMENTS

| 5,089,833 | A | 2/1992 | Takahashi |
| 5,116,964 | A | 5/1992 | Capon |
| 5,155,027 | A | 10/1992 | Sledziewski |
| 5,336,603 | A | 8/1994 | Capon |
| 5,567,584 | A | 10/1996 | Sledziewski |
| 5,712,380 | A | 1/1998 | Kendall |
| 5,827,702 | A | 10/1998 | Cuthbertson |
| 5,843,725 | A | 12/1998 | Sledziewski |
| 6,100,071 | A | 8/2000 | Davis-Smyth |
| 6,204,011 | B1 | 3/2001 | Kendall |
| 6,270,993 | B1 | 8/2001 | Shibuya |
| 6,348,333 | B1 | 2/2002 | Niwa |
| 6,375,929 | B1 | 4/2002 | Thomas, Jr. |
| 6,378,526 | B1 | 4/2002 | Bowman |
| 6,383,486 | B1 | 5/2002 | Davis-Smyth |
| 6,397,849 | B1 | 6/2002 | Bowman |
| 6,482,634 | B1 | 11/2002 | Wilson |
| 6,686,200 | B1 | 2/2004 | Dong |
| 6,821,775 | B1 | 11/2004 | Kovesdi |
| 6,897,294 | B2 | 5/2005 | Davis-Smyth |
| 6,943,019 | B2 | 9/2005 | Wilson |
| 6,943,153 | B1 | 9/2005 | Manning |
| 7,083,950 | B2 | 8/2006 | Stahl |
| 7,087,411 | B2 | 8/2006 | Daly |
| 2002/0098187 | A1 | 7/2002 | Ferrara |
| 2003/0092604 | A1 | 5/2003 | Davis-Smyth et al. |
| 2004/0052785 | A1 | 3/2004 | Goodman |
| 2005/0163798 | A1 | 7/2005 | Papadopoulos |
| 2005/0175624 | A1 | 8/2005 | Romero |
| 2006/0134111 | A1 | 6/2006 | Agarwal |
| 2006/0193830 | A1 | 8/2006 | Hauswirth |

FOREIGN PATENT DOCUMENTS

| EP | 0928203 | | 7/1999 |
| EP | 1238986 | A2 | 9/2002 |
| EP | 1621213 | | 2/2006 |
| WO | WO9108298 | A2 | 6/1991 |
| WO | WO9410202 | A1 | 5/1994 |
| WO | WO9421679 | A1 | 9/1994 |
| WO | WO9506743 | A2 | 3/1995 |
| WO | WO9613276 | A1 | 5/1996 |
| WO | WO 98/13071 | | 4/1998 |
| WO | WO9831794 | A1 | 7/1998 |
| WO | WO 98/51323 | | 11/1998 |
| WO | WO9855638 | A1 | 12/1998 |
| WO | WO9858053 | A1 | 12/1998 |
| WO | WO0054813 | A2 | 9/2000 |
| WO | WO0075319 | A1 | 12/2000 |
| WO | WO0224234 | A2 | 3/2002 |
| WO | WO03080648 | A2 | 10/2003 |
| WO | WO 2004/085478 | | 10/2004 |
| WO | WO2006066086 | A1 | 6/2006 |

OTHER PUBLICATIONS

Lai, YKY et al., "Potential long-term inhibition of ocular neovascularisation by recombinant adeno-associated virus-mediated secretion gene therapy", Gene Therapy, 9:804-813, 2002.

Mori, K. et al., "AAV-Mediated Gene Transfer of Pigment Epithelium-Derived Factor Inhibits Choroidal Neovascularization", Investigative Opthalmology & Visual Science, 43(6):1994-2000, Jun. 2002.

(Continued)

*Primary Examiner* — Marianne P Allen
(74) *Attorney, Agent, or Firm* — Roberta L. Robins; Robins Law Group

(57) ABSTRACT

Multimeric fusion proteins of an Ig-like domain of Flt-1 are rendered functional by inclusion of a linker moiety. Vectors encoding the fusion proteins and host cells expressing the fusion proteins can be used therapeutically to block neovascularization in individuals with pathological conditions related to neovascularization. Such conditions include age-related macular degeneration, cancer, psoriasis, proliferative diabetic retinopathy, asthma, uveitis, osteoarthritis, and rheumatoid arthritis. The same means of multimerization used for an Iglike domain of Flt-1, i.e., a linker and a multimerization domain, can be used for other polypeptides, including extracellular receptors, antibody variable regions, cytokines, chemokines, and growth factors.

28 Claims, 14 Drawing Sheets

(56) References Cited

OTHER PUBLICATIONS

Campochiaro, Peter A., "Gene therapy for retinal and choroidal diseases", Expert Opin. Biol. Ther., 2(5):537-544, 2002.
Chaum, E. and Hatton, M.P., "Gene Therapy for Genetic and Acquired Retinal Diseases", Survey of Opthalmology, 47(5):449-469, Sep.-Oct. 2002.
Borras, Teresa, "Recent developments in ocular gene therapy", Experimental Eye Research, 76:643-652, 2003.
Pleyer, U. and Ritter, T., "Gene therapy in immune-mediated diseases of the eye", Progress in Retinal and Eye Research, 22:277-293, 2003.
Jomary, C. et al., "Adenoassociated Virus Vector-Mediated Gene Transfer to Retinal Cells In Vitro and In Vivo", Investigative Ophthalmology & Visual Science, 36(4):Abstract 3569-556, Mar. 15, 1995.
Ali, R.R. et al., "Gene transfer into the mouse retina mediated by an adeno-associated viral vector", Human Molecular Genetics, 5(5):591-594, 1996.
Hauswirth, W. et al., "Efficient Photoreceptor-Targeted Gene Expression In Vivo Mediated by Recombinant Adeno-Associated Virus", Investigative Ophthalmology & Visual Science, 38(4): Abstract 1193-5:45, Mar. 15, 1997.
Bennett, J. et al., "Real-Time, Noninvasive In Vivo Assessment of Adeno-Associated Virus-Mediated Retinal Transduction", Investigative Ophthalmology & Visual Science, 38:(13):2857-2863, Dec. 1997.
Ali, R.R. et al., "Adeno-Associated Virus Gene Transfer to Mouse Retina", Human Gene Therapy, 9:81-86, Jan. 1, 1998.
Bennett, J. et al., "Stable transgene expression in rod photoreceptors after recombinant adeno-associated virus-mediated gene transfer to monkey retina", Proc. Natl. Acad. Sci., USA, 96:9920-9925, Aug. 1999.
Auricchio, A. et al., "Inhibition of Retinal Neovascularization by Intraocular Viral-Mediated Delivery of Anti-angiogenic Agents", Molecular Therapy, 6(4):490-494, Oct. 2002.
Bok, Dean, "Retinal Transplantation and Gene Therapy", Investigative Ophthalmology & Visual Science, 34(3):473-476, Mar. 1993.
Zack, Donald J., "Ocular Gene Therapy From Fantasy to Forseeable Reality", Arch Ophthalmology, 111:1477-1478, Nov. 1993.
Bennett, J., "Immune response following introcular delivery of recombinant viral vectors", Gene Therapy, 10:977-982, 2003.
National Institutes of Health Recombinant DNA Advisory Committee (RAC Meeting) Sep. 6-7, 2001, Meeting Agenda, Human Gene Therapy 12:2021-2032, Nov. 1, 2001.
Mashhour, B. et al., "In vivo adenovirus-mediated gene transfer into ocular tissues", Gene Therapy, 1:122-126, 1994.
Li, T. et al., "In Vivo Transfer of a Reporter Gene to the Retina Mediated by an Adenoviral Vector", Investigative Ophthalmology & Visual Science, 35(5):2543-2549, Apr. 1994.
Jomary, C. et al., "Adenovirus-mediated gene transfer to murine retinal cells in vitro and in vivo", FEBS Letters, 347:117-122, 1994.
Bennett, J. et al., "Adenovirus Vector-Mediated In Vivo Gene Transfer Into Adult Murine Retina", Investigative Ophthalmology & Visual Science, 35(5):2535-2542, 1994.

Mahasreshti, P.J. et al., "Adenovirus-mediated Soluble FLT-1 Gene Therapy for Ovarian Carcinoma", Clinical Cancer Research, 7:2057-2066, Jul. 2001.
Dejneka, NS et al., "Pharmacologically regulated gene expression in the retinal following transduction with viral vectors", Gene Therapy, 8:442-446, 2001.
Cunningham, S.A. et al., "Identification of the Extracellular Domains of Flt-1 That Mediate Ligand Interactions", Biochemical and Biophysical Research Communications 231:596-599, 1997.
Harris, Adrian L., "von Hippel-Lindau Syndrome: Target for Anti-Vascular Endothelial Growth Factor (VEGF) Receptor Therapy", The Oncologist, 5(suppl 1):32-36, 2000.
Weismann, C. et al., "Crystal Structure at 1.7 A Resolution of VEGF in Complex with Domain 2 of the Flt-1 Receptor", Cell, 91:695-704, Nov. 28, 1997.
Bainbridge, JWB et al., "Inhibition of retinal neovascularisation by gene transfer of soluble VEGF receptor sFlt-1", Gene Therapy, 9:320-326, 2002.
Gerber, Hans-Peter et al., "Complete Inhibition of Rhabdomyosarcoma Xenograft Growth and Neovascularization Requires Blockade of Both Tumor and Host Vascular Endothelial Growth Factor", Cancer Research, 60:6253-6258, Nov. 15, 2000.
Hu, Shi-zhen et al., "Minibody: A Novel Engineered Anti-Carcinoembryonic Antigen Antibody Fragment (Single-Chain Fv-CH3) Which Exhibits Rapid, High-Level Targeting of Xenografts", Cancer Research, 56:3055-3061, Jul. 1, 1996.
Lai, Chooi-May et al., "Long-Term Evaluation of AAV-Mediated sFlt-1 Gene Therapy for Ocular Neovascularization in Mice and Monkeys", Molecular Therapy, 12(4):659-668, Oct. 2005.
Li, Erqiu et al., "Mammalian cell expression of dimeric small immune proteins (SIP)", Protein Engineering, 10:(6):731-736, 1997.
Thompson, Jerry et al., "Improved binding of a bivalent single-chain immunotoxin results in increased efficacy for in vivo T-cell depletion", Protein Engineering, 14(12):1035-1041, 2001.
Kendall, R.L. and Thomas, K.A., "Inhibition of vascular endothelial cell growth factor activity by an endogenously encoded soluble receptor", Proc. Natl. Acad. Sci. USA, 90:10705-10709, Nov. 1993.
Holash, J. et al., "VEGF-Trap: A VEGF blocker with potent antitumor effects", Proceeding of the National Academy of Sciences of USA, 99(17):11393-11398, Aug. 20, 2002.
Vangelista, L. et al., "A minimal receptor-Ig chimera of human FcepsilonRI alpha-chain efficiently binds secretory and membrane IgE", Protein Engineering, 15(1):51-57, Jan. 2002.
Olafsen, T. et al., "Characterization of engineered anti-p185HER-2 (scFv-CH3) 2 antibody fragments (minibodies) for tumor targeting", Protein Engineering Design & Selection, 17(4):315-323, Apr. 2004.
Hu, S-Z et al., "Minibody: A Novel Engineered Anti-Carcinoembryonic Antigen Antibody Fragment (Single-chain FV-CH3) which Exhibits Rapid, High-Level Targeting of Xenografts", Cancer Research, 56(13):3055-3061, Jul. 1, 1996.
Afanasieva T.A. et al., "Single-chain antibody and its derivatives directed against vascular endothelial growth factor: application for antiangiogenic gene therapy", Gene Therapy, 10(21):1850-1859, Oct. 1, 2003.

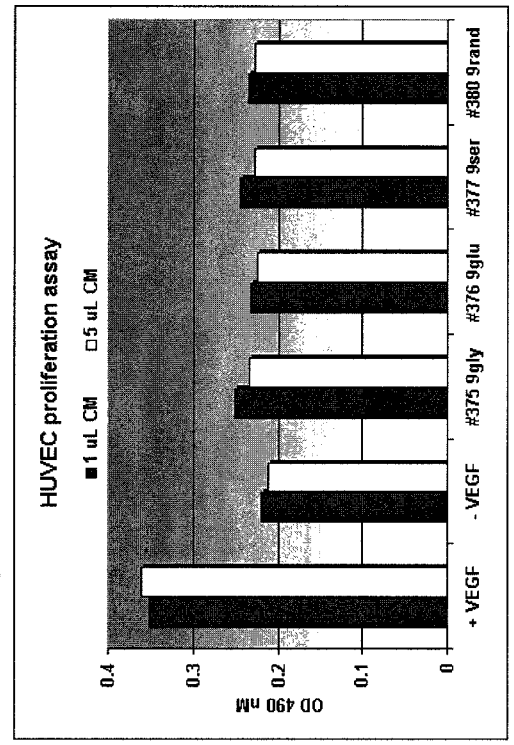
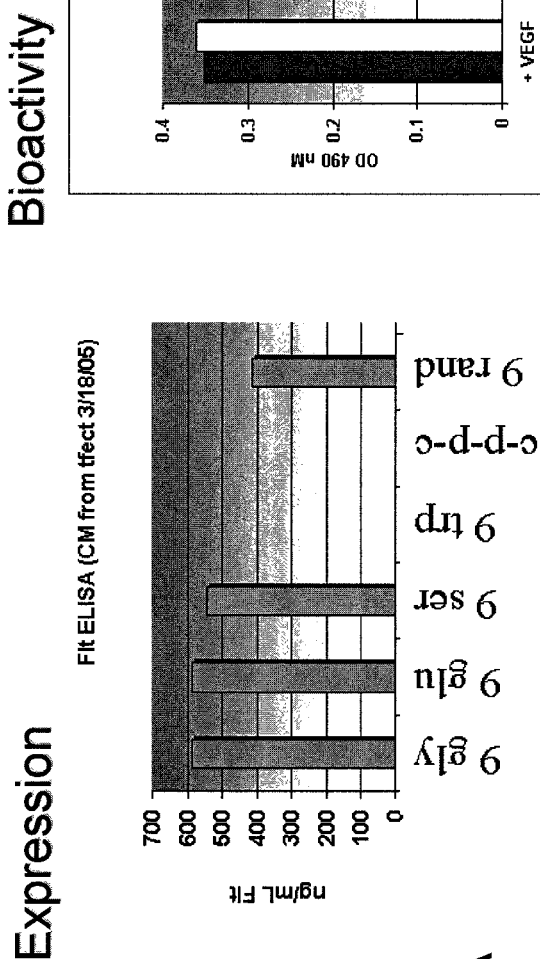
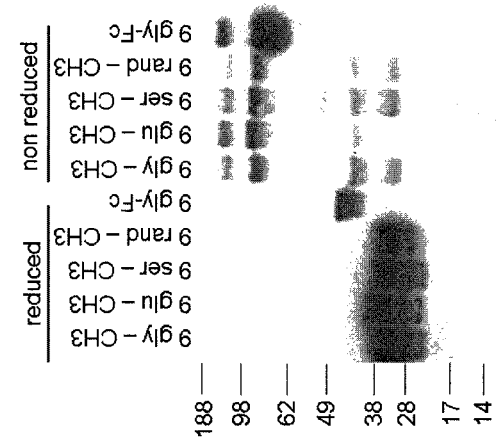
FIG 13 A
FIG 13 B
FIG 13 C

SEQUENCE LISTING

```
<160> NUMBER OF SEQ ID NOS: 34

<210> SEQ ID NO 1
<211> LENGTH: 1077
<212> TYPE: DNA
<213> ORGANISM: Artificial Sequence
<220> FEATURE:
<223> OTHER INFORMATION: Recombinant fusion protein or sequence encoding
      same

<400> SEQUENCE: 1
atggtcagct actgggacac cggggtcctg ctgtgcgcgc tgctcagctg tctgcttctc      60
acaggatctg gtagaccttt cgtagagatg tacagtgaaa tccccgaaat tatacacatg     120
actgaaggaa gggagctcgt cattccctgc cgggttacgc acctaacat cactgttact      180 ttaaaaagt tccacttga cactttgatc cctgatggaa aacgcataat ctgggacagt       240
agaaagggct tcatcatatc aaatgcaacg tacaaagaaa tagggcttct gacctgtgaa     300
gcaacagtca atgggcattt gtataagaca aactatctca cacatcgaca aaccggtgga    360
ggtggaggtg gaggtggagg tcctaaatct tgtgacaaaa ctcacacatg cccaccgtgc     420
ccagcacctg aactcctggg gggaccgtca gtcttcctct tccccccaaa acccaaggac     480
accctcatga tctcccggac ccctgaggtc acatgcgtgg tggtggacgt gagccacgaa     540
```

```
gaccctgagg tcaagttcaa ctggtacgtg gacggcgtgg aggtgcataa tgccaagaca    600
aagccgcggg aggagcagta caacagcacg taccgtgtgg tcagcgtcct caccgtcctg    660
caccaggact ggctgaatgg caaggagtac aagtgcaagg tctccaacaa agccctccca    720
gcccccatcg agaaaaccat ctccaaagcc aagggcagc cccgagaacc acaggtgtac     780
accctgcccc catcccggga tgagctgacc aagaaccagg tcagcctgac ctgcctggtc    840
aaaggcttct atcccagcga catcgccgtg gagtgggaga gcaatgggca gccggagaac    900
aactacaaga ccacgcctcc cgtgctggac tccgacggct ccttcttcct ctacagcaag    960
ctcaccgtgg acaagagcag gtggcagcag gggaacgtct tctcatgctc cgtgatgcat   1020
gaggctctgc acaaccacta cacgcagaag agcctctccc tgtctccggg taaatag     1077
```

<210> SEQ ID NO 2
<211> LENGTH: 358
<212> TYPE: PRT
<213> ORGANISM: Artificial Sequence
<220> FEATURE:
<223> OTHER INFORMATION: Recombinant fusion protein or sequence encoding
      same

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Gly Arg Pro Phe Val Glu Met Tyr Ser
            20                  25                  30

Glu Ile Pro Glu Ile Ile His Met Thr Glu Gly Arg Glu Leu Val Ile
        35                  40                  45

Pro Cys Arg Val Thr Ser Pro Asn Ile Thr Val Thr Leu Lys Lys Phe
    50                  55                  60

Pro Leu Asp Thr Leu Ile Pro Asp Gly Lys Arg Ile Ile Trp Asp Ser
65                  70                  75                  80

Arg Lys Gly Phe Ile Ile Ser Asn Ala Thr Tyr Lys Glu Ile Gly Leu
                85                  90                  95

Leu Thr Cys Glu Ala Thr Val Asn Gly His Leu Tyr Lys Thr Asn Tyr
            100                 105                 110

Leu Thr His Arg Gln Thr Gly Gly Gly Gly Gly Gly Gly Gly Gly Pro
        115                 120                 125

Lys Ser Cys Asp Lys Thr His Thr Cys Pro Pro Cys Pro Ala Pro Glu
    130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270
```

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
        290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
            355

<210> SEQ ID NO 3
<211> LENGTH: 1050
<212> TYPE: DNA
<213> ORGANISM: Artificial Sequence
<220> FEATURE:
<223> OTHER INFORMATION: Recombinant fusion protein or sequence encoding
      same

<400> SEQUENCE: 3
atggtcagct actgggacac cggggtcctg ctgtgcgcgc tgctcagctg tctgcttctc      60
acaggatctg gtagaccttt cgtagagatg tacagtgaaa tccccgaaat tatacacatg     120
actgaaggaa gggagctcgt cattccctgc cgggttacgt cacctaacat cactgttact     180
ttaaaaaagt ttccacttga cactttgatc cctgatggaa aacgcataat ctgggacagt     240
agaaagggct tcatcatatc aaatgcaacg tacaaagaaa tagggcttct gacctgtgaa     300
gcaacagtca tgggcatttt gtataagaca aactatctca cacatcgaca aacccctaaa     360
tcttgtgaca aaactcacac atgcccaccg tgcccagcac ctgaactcct ggggggaccg     420
tcagtcttcc tcttcccccc aaaacccaag gacaccctca tgatctcccg gacccctgag     480
gtcacatgcg tggtggtgga cgtgagccac gaagaccctg aggtcaagtt caactggtac     540
gtggacggcg tggaggtgca taatgccaag acaaagccgc gggaggagca gtacaacagc     600
acgtaccgtg tggtcagcgt cctcaccgtc ctgcaccagg actggctgaa tggcaaggag     660
tacaagtgca aggtctccaa caaagccctc ccagccccca tcgagaaaac catctccaaa     720
gccaaagggc agccccgaga accacaggtg tacaccctgc ccccatcccg ggatgagctg     780
accaagaacc aggtcagcct gacctgcctg gtcaaaggct tctatcccag cgacatcgcc     840
gtggagtggg agagcaatgg gcagccggag aacaactaca agaccacgcc tcccgtgctg     900
gactccgacg gctccttctt cctctacagc aagctcaccg tggacaagag caggtggcag     960
caggggaacg tcttctcatg ctccgtgatg catgaggctc tgcacaacca ctacacgcag    1020
aagagcctct ccctgtctcc gggtaaatag                                     1050

<210> SEQ ID NO 4
<211> LENGTH: 349
<212> TYPE: PRT
<213> ORGANISM: Artificial Sequence
<220> FEATURE:
<223> OTHER INFORMATION: Recombinant fusion protein or sequence encoding
      same

<400> SEQUENCE: 4

Met Val Ser Tyr Trp Asp Thr Gly Val Leu Leu Cys Ala Leu Leu Ser
1               5                   10                  15

Cys Leu Leu Leu Thr Gly Ser Gly Arg Pro Phe Val Glu Met Tyr Ser
            20                  25                  30

Glu Ile Pro Glu Ile Ile His Met Thr Glu Gly Arg Glu Leu Val Ile
        35                  40                  45

Pro Cys Arg Val Thr Ser Pro Asn Ile Thr Val Thr Leu Lys Lys Phe
50                  55                  60

Pro Leu Asp Thr Leu Ile Pro Asp Gly Lys Arg Ile Ile Trp Asp Ser
65                  70                  75                  80

Arg Lys Gly Phe Ile Ile Ser Asn Ala Thr Tyr Lys Glu Ile Gly Leu
                85                  90                  95

Leu Thr Cys Glu Ala Thr Val Asn Gly His Leu Tyr Lys Thr Asn Tyr
            100                 105                 110

Leu Thr His Arg Gln Thr Pro Lys Ser Cys Asp Lys Thr His Thr Cys
        115                 120                 125

Pro Pro Cys Pro Ala Pro Glu Leu Leu Gly Gly Pro Ser Val Phe Leu
130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Asp Glu Leu Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys
            340                 345

<210> SEQ ID NO 5
<211> LENGTH: 426
<212> TYPE: DNA
<213> ORGANISM: Artificial Sequence
<220> FEATURE:
<223> OTHER INFORMATION: Recombinant fusion protein or sequence encoding
      same -continued

<400> SEQUENCE: 5

```
atggtcagct actgggacac cggggtcctg ctgtgcgcgc tgctcagctg tctgcttctc      60
acaggatctg gtagacctt cgtagagatg tacagtgaaa tccccgaaat tatacacatg     120
actgaaggaa gggagctcgt cattccctgc cgggttacgt cacctaacat cactgttact    180
ttaaaaaagt ttccacttga cactttgatc cctgatggaa aacgcataat ctgggacagt   240
agaaagggct tcatcatatc aaatgcaacg tacaaagaaa tagggcttct gacctgtgaa   300
gcaacagtca atgggcattt gtataagaca aactatctca cacatcgaca aaccggtgga   360
ggtggaggtg gaggtggagg tccttcctgt gtgcccctga tgcgatgcgg gggctgctgc   420
aattag                                                               426
```

<210> SEQ ID NO 6
<211> LENGTH: 141
<212> TYPE: PRT
<213> ORGANISM: Artificial Sequence
<220> FEATURE:
<223> OTHER INFORMATION: Recombinant fusion protein or sequence encoding same

<400> SEQUENCE: 6

```
Met Val Ser Tyr Trp Asp Thr Gly Val Leu Leu Cys Ala Leu Leu Ser
1               5                   10                  15
Cys Leu Leu Leu Thr Gly Ser Gly Arg Pro Phe Val Glu Met Tyr Ser
            20                  25                  30
Glu Ile Pro Glu Ile Ile His Met Thr Glu Gly Arg Glu Leu Val Ile
        35                  40                  45
Pro Cys Arg Val Thr Ser Pro Asn Ile Thr Val Thr Leu Lys Lys Phe
    50                  55                  60
Pro Leu Asp Thr Leu Ile Pro Asp Gly Lys Arg Ile Ile Trp Asp Ser
65                  70                  75                  80
Arg Lys Gly Phe Ile Ile Ser Asn Ala Thr Tyr Lys Glu Ile Gly Leu
                85                  90                  95
Leu Thr Cys Glu Ala Thr Val Asn Gly His Leu Tyr Lys Thr Asn Tyr
            100                 105                 110
Leu Thr His Arg Gln Thr Gly Gly Gly Gly Gly Gly Gly Gly Gly Pro
        115                 120                 125
Ser Cys Val Pro Leu Met Arg Cys Gly Gly Cys Cys Asn
    130                 135                 140
```

<210> SEQ ID NO 7
<211> LENGTH: 744
<212> TYPE: DNA
<213> ORGANISM: Artificial Sequence
<220> FEATURE:
<223> OTHER INFORMATION: Recombinant fusion protein or sequence encoding same

<400> SEQUENCE: 7

```
atggtcagct actgggacac cggggtcctg ctgtgcgcgc tgctcagctg tctgcttctc      60
acaggatctg gtagacctt cgtagagatg tacagtgaaa tccccgaaat tatacacatg     120
actgaaggaa gggagctcgt cattccctgc cgggttacgt cacctaacat cactgttact    180
ttaaaaaagt ttccacttga cactttgatc cctgatggaa aacgcataat ctgggacagt   240
agaaagggct tcatcatatc aaatgcaacg tacaaagaaa tagggcttct gacctgtgaa   300
gcaacagtca atgggcattt gtataagaca aactatctca cacatcgaca aaccggtgga   360
ggtggaggtg gaggtggagg tccttcctgt gtgcccctga tgcgatgcgg gggctgctgc   420
```

```
aatcagcccc gagaaccaca ggtgtacacc ctgcccccat cccgggatga gctgaccaag    480
aaccaggtca gcctgacctg cctggtcaaa ggcttctatc ccagcgacat cgccgtggag    540
tgggagagca atgggcagcc ggagaacaac tacaagacca cgcctcccgt gctggactcc    600
gacggctcct tcttcctcta cagcaagctc accgtggaca gagcaggtg gcagcagggg    660 aacgtcttct catgctccgt gatgcatgag gctctgcaca accactacac gcagaagagc    720 ctctcccctgt ctccgggtaa atag                                          744
```

```
<210> SEQ ID NO 8
<211> LENGTH: 247
<212> TYPE: PRT
<213> ORGANISM: Artificial Sequence
<220> FEATURE:
<223> OTHER INFORMATION: Recombinant fusion protein or sequence encoding
      same

<400> SEQUENCE: 8
```

Met Val Ser Tyr Trp Asp Thr Gly Val Leu Leu Cys Ala Leu Leu Ser
1               5                   10                  15

Cys Leu Leu Leu Thr Gly Ser Gly Arg Pro Phe Val Glu Met Tyr Ser
            20                  25                  30

Glu Ile Pro Glu Ile Ile His Met Thr Glu Gly Arg Glu Leu Val Ile
        35                  40                  45

Pro Cys Arg Val Thr Ser Pro Asn Ile Thr Val Thr Leu Lys Lys Phe
    50                  55                  60

Pro Leu Asp Thr Leu Ile Pro Asp Gly Lys Arg Ile Ile Trp Asp Ser
65                  70                  75                  80

Arg Lys Gly Phe Ile Ile Ser Asn Ala Thr Tyr Lys Glu Ile Gly Leu
                85                  90                  95

Leu Thr Cys Glu Ala Thr Val Asn Gly His Leu Tyr Lys Thr Asn Tyr
            100                 105                 110

Leu Thr His Arg Gln Thr Gly Gly Gly Gly Gly Gly Gly Gly Gly Pro
        115                 120                 125

Ser Cys Val Pro Leu Met Arg Cys Gly Gly Cys Cys Asn Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245

```
<210> SEQ ID NO 9
<211> LENGTH: 1434
<212> TYPE: DNA
<213> ORGANISM: Homo sapiens
```

<400> SEQUENCE: 9

```
atggagtttg ggctgagctg ggttttcctc gttgctcttt taagaggtgt ccagtgtcag    60
gtgcagctgg tggagtctgg gggaggcgtg gtccagcctg gaggtccct gagactctcc    120
tgtgcagcgt ctggattcac cttcagtaat tatggcatgc actgggtccg ccaggctcca   180
ggcaaggggc tggagtgggt ggcagctata tggtatgatg gaagtaataa atactatgca   240
gactccgtga agggccgatt caccatctcc agagacaatt ccaagaacac gttgtatatg   300
caaatgaaca gcctgagagc cgaggacacg gctgtgtatt attgtgcgag agagggtcgg   360
tgggtacgat atactacggt gactactatc ggatactact ttgactactg gggccaggga   420
accctggtca ccgtctcctc agcctccacc aagggcccat cggtcttccc cctggcaccc   480
tcctccaaga gcacctctgg gggcacagcg gccctgggct gcctggtcaa ggactacttc   540
cccgaaccgg tgacggtgtc gtggaactca ggcgccctga ccagcggcgt gcacaccttc   600
ccggctgtcc tacagtcctc aggactctac tccctcagca gcgtggtgac cgtgccctcc   660
agcagcttgg gcacccagac ctacatctgc aacgtgaatc acaagcccag caacaccaag   720
gtggacaaga gagttgagcc caaatcttgt gacaaaactc acacatgccc accgtgccca   780
gcacctgaac tcctgggggg accgtcagtc ttcctcttcc cccaaaaacc caaggacacc   840
ctcatgatct cccggacccc tgaggtcaca tgcgtggtgg tggacgtgag ccacgaagac   900
cctgaggtca agttcaactg gtacgtggac ggcgtggagg tgcataatgc caagacaaag   960
ccgcgggagg agcagtacaa cagcacgtac cgtgtggtca gcgtcctcac cgtcctgcac  1020
caggactggc tgaatggcaa ggagtacaag tgcaaggtct ccaacaaagc cctcccagcc  1080
cccatcgaga aaaccatctc caaagccaaa gggcagcccc gagaaccaca ggtgtacacc  1140
ctgcccccat cccgggagga gatgaccaag aaccaggtca gcctgacctg cctggtcaaa  1200
ggcttctatc ccagcgacat cgccgtggag tgggagagca atgggcagcc ggagaacaac  1260
tacaagacca cgcctcccgt gctggactcc gacggctcct tcttcctcta tagcaagctc  1320
accgtggaca agagcaggtg gcagcagggg aacgtcttct catgctccgt gatgcatgag  1380
gctctgcaca accactacac gcagaagagc ctctccctgt ccccgggtaa atga         1434
```

<210> SEQ ID NO 10
<211> LENGTH: 477
<212> TYPE: PRT
<213> ORGANISM: Homo sapiens

<400> SEQUENCE: 10

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Gly Met His Trp Val Arg Gln Ala Pro Gly Lys Gly Leu
    50                  55                  60

Glu Trp Val Ala Ala Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Met Gln Met Asn Ser Leu Arg Ala Glu Asp Thr Ala Val
            100                 105                 110
```

```
Tyr Tyr Cys Ala Arg Glu Gly Arg Trp Val Arg Tyr Thr Thr Val Thr
        115                 120                 125

Thr Ile Gly Tyr Tyr Phe Asp Tyr Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Arg Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475

<210> SEQ ID NO 11
<211> LENGTH: 648
<212> TYPE: DNA
<213> ORGANISM: Homo sapiens

<400> SEQUENCE: 11
atgaactttc tgctgtcttg ggtgcattgg agccttgcct tgctgctcta cctccaccat      60
gccaagtggt cccaggctgc acccatggca gaaggaggag ggcagaatca tcacgaagtg     120
```

```
gtgaagttca tggatgtcta tcagcgcagc tactgccatc caatcgagac cctggtggac      180
atcttccagg agtaccctga tgagatcgag tacatcttca agccatcctg tgtgcccctg      240
atgcgatgcg ggggctgctg caatgacgag ggcctggagt gtgtgcccac tgaggagtcc      300
aacatcacca tgcagattat gcggatcaaa cctcaccaag ccagcacat aggagagatg       360 agcttcctac agcacaacaa atgtgaatgc agaccaaaga agatagagc aagacaagaa       420 aaaaaatcag ttcgaggaaa gggaaagggg caaaaacgaa agcgcaagaa atcccggtat      480
aagtcctgga gcgttccctg tgggccttgc tcagagcgga gaaagcattt gtttgtacaa      540
gatccgcaga cgtgtaaatg ttcctgcaaa aacacagact cgcgttgcaa ggcgaggcag      600
cttgagttaa acgaacgtac ttgcagatgt gacaagccga ggcggtga                   648
```

<210> SEQ ID NO 12
<211> LENGTH: 215
<212> TYPE: PRT
<213> ORGANISM: Homo sapiens

<400> SEQUENCE: 12

```
Met Asn Phe Leu Leu Ser Trp Val His Trp Ser Leu Ala Leu Leu
 1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Arg Cys Asp Lys Pro Arg Arg
    210                 215
```

<210> SEQ ID NO 13
<211> LENGTH: 14
<212> TYPE: PRT
<213> ORGANISM: Homo sapiens

<400> SEQUENCE: 13

```
Pro Ser Cys Val Pro Leu Met Arg Cys Gly Gly Cys Cys Asn
 1               5                  10
```

<210> SEQ ID NO 14
<211> LENGTH: 5777
<212> TYPE: DNA
<213> ORGANISM: Homo sapiens

<400> SEQUENCE: 14

| | | | | | |
|---|---|---|---|---|---|
| gcggacactc | ctctcggctc | ctccccggca | gcggcggcgg | ctcggagcgg | gctccggggc | 60 |
| tcgggtgcag | cggccagcgg | gcctggcggc | gaggattacc | cggggaagtg | gttgtctcct | 120 |
| ggctggagcc | gcgagacggg | cgctcagggc | gcggggccgg | cggcggcgaa | cgagaggacg | 180 |
| gactctggcg | gccgggtcgt | tggcggggg | agcgcgggca | ccgggcgagc | aggccgcgtc | 240 |
| gcgctcacca | tggtcagcta | ctgggacacc | ggggtcctgc | tgtgcgcgct | gctcagctgt | 300 |
| ctgcttctca | caggatctag | ttcaggttca | aaattaaaag | atcctgaact | gagttttaaaa | 360 |
| ggcacccagc | acatcatgca | agcaggccag | acactgcatc | tccaatgcag | ggggaagca | 420 |
| gcccataaat | ggtctttgcc | tgaaatggtg | agtaaggaaa | gcgaaaggct | gagcataact | 480 |
| aaaatctgcct | gtgaagaaa | tggcaaacaa | ttctgcagta | ctttaacctt | gaacacagct | 540 |
| caagcaaacc | acactggctt | ctacagctgc | aaatatctag | ctgtacctac | ttcaaagaag | 600 |
| aaggaaacag | aatctgcaat | ctatatattt | attagtgata | caggtagacc | tttcgtagag | 660 |
| atgtacagtg | aaatccccga | aattatacac | atgactgaag | gaagggagct | cgtcattccc | 720 |
| tgccgggtta | cgtcacctaa | catcactgtt | actttaaaaa | agtttccact | tgacactttg | 780 |
| atccctgatg | gaaaacgcat | aatctgggac | agtagaaagg | gcttcatcat | atcaaatgca | 840 |
| acgtacaaag | aaatagggct | tctgacctgt | gaagcaacag | tcaatgggca | tttgtataag | 900 |
| acaaactatc | tcacacatcg | acaaaccaat | acaatcatag | atgtccaaat | aagcacacca | 960 |
| cgcccagtca | aattacttag | aggccatact | cttgtcctca | attgtactgc | taccactccc | 1020 |
| ttgaacacga | gagttcaaat | gacctggagt | taccctgatg | aaaaaaataa | gagagcttcc | 1080 |
| gtaaggcgac | gaattgacca | aagcaattcc | catgccaaca | tattctacag | tgttcttact | 1140 |
| attgacaaaa | tgcagaacaa | agacaaagga | ctttatactt | gtcgtgtaag | gagtggacca | 1200 |
| tcattcaaat | ctgttaacac | ctcagtgcat | atatatgata | aagcattcat | cactgtgaaa | 1260 |
| catcgaaaac | agcaggtgct | tgaaaccgta | gctggcaagc | ggtcttaccg | gctctctatg | 1320 |
| aaagtgaagg | catttccctc | gccggaagtt | gtatggttaa | agatgggtt | acctgcgact | 1380 |
| gagaaatctg | ctcgctattt | gactcgtggc | tactcgttaa | ttatcaagga | cgtaactgaa | 1440 |
| gaggatgcag | ggaattatac | aatcttgctg | agcataaaac | agtcaaatgt | gtttaaaaac | 1500 |
| ctcactgcca | ctctaattgt | caatgtgaaa | ccccagattt | acgaaaaggc | cgtgtcatcg | 1560 |
| tttccagacc | cggctctcta | cccactgggc | agcagacaaa | tcctgacttg | taccgcatat | 1620 |
| ggtatccctc | aacctacaat | caagtggttc | tggcacccct | gtaaccataa | tcattccgaa | 1680 |
| gcaaggtgtg | acttttgttc | caataatgaa | gagtccttta | tcctggatgc | tgacagcaac | 1740 |
| atgggaaaca | gaattgagag | catcactcag | cgcatggcaa | taatagaagg | aaagaataag | 1800 |
| atggctagca | ccttggttgt | ggctgactct | agaatttctg | gaatctacat | ttgcatagct | 1860 |
| tccaataaag | ttgggactgt | gggaagaaac | ataagctttt | atatcacaga | tgtgccaaat | 1920 |
| gggtttcatg | ttaacttgga | aaaaatgccg | acggaaggag | aggacctgaa | actgtcttgc | 1980 |
| acagttaaca | agttccttta | cagagacgtt | acttggattt | tactgcggac | agttaataac | 2040 |
| agaacaatgc | actacagtat | tagcaagcaa | aaaatggcca | tcactaagga | gcactccatc | 2100 |
| actcttaatc | ttaccatcat | gaatgttccc | ctgcaagatt | caggcaccta | tgcctgcaga | 2160 |
| gccaggaatg | tatacacagg | ggaagaaatc | ctccagaaga | aagaaattac | aatcagagat | 2220 |

```
caggaagcac catacctcct gcgaaacctc agtgatcaca cagtggccat cagcagttcc    2280
accactttag actgtcatgc taatggtgtc cccgagcctc agatcacttg gtttaaaaac    2340
aaccacaaaa tacaacaaga gcctggaatt attttaggac caggaagcag cacgctgttt    2400
attgaaagag tcacagaaga ggatgaaggt gtctatcact gcaaagccac caaccagaag    2460
ggctctgtgg aaagttcagc atacctcact gttcaggaa cctcggacaa gtctaatctg    2520
gagctgatca ctctaacatg cacctgtgtg gctgcgactc tcttctggct cctattaacc    2580
ctccttatcc gaaaaatgaa aaggtcttct tctgaaataa agactgacta cctatcaatt    2640
ataatggacc cagatgaagt tcctttggat gagcagtgtg agcggctccc ttatgatgcc    2700
agcaagtggg agtttgcccg ggagagactt aaactgggca atcacttgg aagaggggct    2760 tttggaaaag tggttcaagc atcagcattt ggcattaaga atcacctac gtgccggact    2820 gtggctgtga aaatgctgaa agagggggcc acggccagcg agtacaaagc tctgatgact    2880
gagctaaaaa tcttgaccca cattggccac catctgaacg tggttaacct gctgggagcc    2940
tgcaccaagc aaggagggcc tctgatggtg attgttgaat actgcaaata tggaaatctc    3000
tccaactacc tcaagagcaa acgtgactta ttttttctca acaaggatgc agcactacac    3060
atggagccta agaaagaaaa aatggagcca ggcctggaac aaggcaagaa accaagacta    3120
gatagcgtca ccagcagcga aagctttgcg agctccggct tcaggaaga taaaagtctg    3180 agtgatgttg aggaagagga ggattctgac ggtttctaca aggagcccat cactatggaa    3240
gatctgattt cttacagttt tcaagtggcc agaggcatgg agttcctgtc ttccagaaag    3300
tgcattcatc gggacctggc agcgagaaac attcttttat ctgagaacaa cgtggtgaag    3360
atttgtgatt ttggccttgc ccgggatatt tataagaacc ccgattatgt gagaaaagga    3420
gatactcgac ttcctctgaa atggatggct cccgaatcta tctttgacaa aatctacagc    3480
accaagagcg acgtgtggtc ttacggagta ttgctgtggg aaatcttctc cttaggtggg    3540
tctccatacc caggagtaca aatggatgag acttttgca gtcgcctgag ggaaggcatg    3600
aggatgagag ctcctgagta ctctactcct gaaatctatc agatcatgct ggactgctgg    3660
cacagagacc caaaagaaag gccaagattt gcagaacttg tggaaaaact aggtgatttg    3720
cttcaagcaa atgtacaaca ggatggtaaa gactacatcc caatcaatgc catactgaca    3780
ggaaatagtg ggtttacata ctcaactcct gccttctctg aggacttctt caaggaaagt    3840
atttcagctc cgaagtttaa ttcaggaagc tctgatgatg tcagatatgt aaatgctttc    3900
aagttcatga gcctggaaag aatcaaaacc tttgaagaac ttttaccgaa tgccacctcc    3960
atgtttgatg actaccaggg cgacagcagc actctgttgg cctctcccat gctgaagcgc    4020
ttcacctgga ctgacagcaa acccaaggcc tcgctcaaga ttgacttgag agtaaccagt    4080
aaaagtaagg agtcggggct gtctgatgtc agcaggccca gtttctgcca ttccagctgt    4140
gggcacgtca gcgaaggcaa gcgcaggttc acctacgacc acgctgagct ggaaaggaa    4200 atcgcgtgct gctcccgcc cccagactac aactcggtgg tcctgtactc cacccccaccc    4260 atctagagtt tgacacgaag ccttatttct agaagcacat gtgtatttat accccccagga    4320 aactagcttt tgccagtatt atgcatatat aagtttacac ctttatcttt ccatgggagc    4380 cagctgctttt ttgtgatttt ttaatagtg ctttttttt ttgactaaca agaatgtaac    4440
tccagataga gaaatagtga caagtgaaga acactactgc taaatcctca tgttactcag    4500
tgttagagaa atccttccta aacccaatga cttccctgct ccaaccccg ccacctcagg    4560 gcacgcagga ccagtttgat tgaggagctg cactgatcac ccaatgcatc acgtaccca    4620
```

-continued

```
ctgggccagc cctgcagccc aaaacccagg gcaacaagcc cgttagcccc agggggatcac   4680 tggctggcct gagcaacatc tcgggagtcc tctagcaggc ctaagacatg tgaggaggaa   4740
aaggaaaaaa agcaaaaagc aagggagaaa agagaaaccg ggagaaggca tgagaaagaa   4800
tttgagacgc accatgtggg cacggagggg gacgggcctc agcaatgcca tttcagtggc   4860
ttcccagctc tgacccttct acatttgagg gcccagccag gagcagatgg acagcgatga   4920
ggggacattt tctggattct gggaggcaag aaaaggacaa atatcttttt tggaactaaa   4980
gcaaatttta gacctttacc tatggaagtg gttctatgtc cattctcatt cgtggcatgt   5040
tttgatttgt agcactgagg gtggcactca actctgagcc catacttttg gctcctctag   5100
taagatgcac tgaaaactta gccagagtta ggttgtctcc aggccatgat ggccttacac   5160
tgaaaatgtc acattctatt ttgggtatta atatatagtc cagacactta actcaatttc   5220
ttggtattat tctgttttgc acagttagtt gtgaaagaaa gctgagaaga atgaaaatgc   5280
agtcctgagg agagttttct ccatatcaaa acgagggctg atggaggaaa aaggtcaata   5340
aggtcaaggg aagacccccgt ctctatacca accaaaccaa ttcaccaaca cagttgggac   5400
ccaaaacaca ggaagtcagt cacgtttcct tttcatttaa tggggattcc actatctcac   5460
actaatctga aggatgtgg aagagcatta gctggcgcat attaagcact ttaagctcct   5520
tgagtaaaaa ggtggtatgt aatttatgca aggtatttct ccagttggga ctcaggatat   5580
tagttaatga gccatcacta gaagaaaagc ccattttcaa ctgctttgaa acttgcctgg   5640
ggtctgagca tgatgggaat agggagacag ggtaggaaag ggcgcctact cttcagggtc   5700
taaagatcaa gtgggccttg gatcgctaag ctggctctgt ttgatgctat ttatgcaagt   5760
tagggtctat gtattta                                                   5777
```

<210> SEQ ID NO 15
<211> LENGTH: 1338
<212> TYPE: PRT
<213> ORGANISM: Homo sapiens
<220> FEATURE:
<221> NAME/KEY: DOMAIN
<222> LOCATION: (235)..(336)
<223> OTHER INFORMATION: domain 3

<400> SEQUENCE: 15

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140
```

```
Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
            165                 170                 175

Leu Ile Pro Asp Gly Lys Arg Ile Ile Trp Asp Ser Arg Lys Gly Phe
        180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
        210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
                340                 345                 350

Tyr Arg Leu Ser Met Lys Val Lys Ala Phe Pro Ser Pro Glu Val Val
                355                 360                 365

Trp Leu Lys Asp Gly Leu Pro Ala Thr Glu Lys Ser Ala Arg Tyr Leu
        370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
        450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
            515                 520                 525

Ile Ser Gly Ile Tyr Ile Cys Ile Ala Ser Asn Lys Val Gly Thr Val
        530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575
```

-continued

```
Cys Thr Val Asn Lys Phe Leu Tyr Arg Asp Val Thr Trp Ile Leu Leu
                580                 585                 590
Arg Thr Val Asn Asn Arg Thr Met His Tyr Ser Ile Ser Lys Gln Lys
            595                 600                 605
Met Ala Ile Thr Lys Glu His Ser Ile Thr Leu Asn Leu Thr Ile Met
610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
Asp Gln Glu Ala Pro Tyr Leu Leu Arg Asn Leu Ser Asp His Thr Val
                660                 665                 670
Ala Ile Ser Ser Ser Thr Thr Leu Asp Cys His Ala Asn Gly Val Pro
            675                 680                 685
Glu Pro Gln Ile Thr Trp Phe Lys Asn Asn His Lys Ile Gln Gln Glu
        690                 695                 700
Pro Gly Ile Ile Leu Gly Pro Gly Ser Ser Thr Leu Phe Ile Glu Arg
705                 710                 715                 720
Val Thr Glu Glu Asp Glu Gly Val Tyr His Cys Lys Ala Thr Asn Gln
                725                 730                 735
Lys Gly Ser Val Glu Ser Ser Ala Tyr Leu Thr Val Gln Gly Thr Ser
            740                 745                 750
Asp Lys Ser Asn Leu Glu Leu Ile Thr Leu Thr Cys Thr Cys Val Ala
        755                 760                 765
Ala Thr Leu Phe Trp Leu Leu Leu Thr Leu Leu Ile Arg Lys Met Lys
770                 775                 780
Arg Ser Ser Ser Glu Ile Lys Thr Asp Tyr Leu Ser Ile Ile Met Asp
785                 790                 795                 800
Pro Asp Glu Val Pro Leu Asp Glu Gln Cys Glu Arg Leu Pro Tyr Asp
                805                 810                 815
Ala Ser Lys Trp Glu Phe Ala Arg Glu Arg Leu Lys Leu Gly Lys Ser
                820                 825                 830
Leu Gly Arg Gly Ala Phe Gly Lys Val Val Gln Ala Ser Ala Phe Gly
            835                 840                 845
Ile Lys Lys Ser Pro Thr Cys Arg Thr Val Ala Val Lys Met Leu Lys
        850                 855                 860
Glu Gly Ala Thr Ala Ser Glu Tyr Lys Ala Leu Met Thr Glu Leu Lys
865                 870                 875                 880
Ile Leu Thr His Ile Gly His His Leu Asn Val Val Asn Leu Leu Gly
                885                 890                 895
Ala Cys Thr Lys Gln Gly Gly Pro Leu Met Val Ile Val Glu Tyr Cys
                900                 905                 910
Lys Tyr Gly Asn Leu Ser Asn Tyr Leu Lys Ser Lys Arg Asp Leu Phe
            915                 920                 925
Phe Leu Asn Lys Asp Ala Ala Leu His Met Glu Pro Lys Lys Glu Lys
        930                 935                 940
Met Glu Pro Gly Leu Glu Gln Gly Lys Lys Pro Arg Leu Asp Ser Val
945                 950                 955                 960
Thr Ser Ser Glu Ser Phe Ala Ser Ser Gly Phe Gln Glu Asp Lys Ser
                965                 970                 975
Leu Ser Asp Val Glu Glu Glu Glu Asp Ser Asp Gly Phe Tyr Lys Glu
                980                 985                 990
Pro Ile Thr Met Glu Asp Leu Ile Ser Tyr Ser Phe Gln Val Ala Arg
            995                1000                1005
```

Gly Met Glu Phe Leu Ser Ser Arg Lys Cys Ile His Arg Asp Leu
1010             1015                 1020

Ala Ala Arg Asn Ile Leu Leu Ser Glu Asn Asn Val Val Lys Ile
1025             1030                 1035

Cys Asp Phe Gly Leu Ala Arg Asp Ile Tyr Lys Asn Pro Asp Tyr
1040             1045                 1050

Val Arg Lys Gly Asp Thr Arg Leu Pro Leu Lys Trp Met Ala Pro
1055             1060                 1065

Glu Ser Ile Phe Asp Lys Ile Tyr Ser Thr Lys Ser Asp Val Trp
1070             1075                 1080

Ser Tyr Gly Val Leu Leu Trp Glu Ile Phe Ser Leu Gly Gly Ser
1085             1090                 1095

Pro Tyr Pro Gly Val Gln Met Asp Glu Asp Phe Cys Ser Arg Leu
1100             1105                 1110

Arg Glu Gly Met Arg Met Arg Ala Pro Glu Tyr Ser Thr Pro Glu
1115             1120                 1125

Ile Tyr Gln Ile Met Leu Asp Cys Trp His Arg Asp Pro Lys Glu
1130             1135                 1140

Arg Pro Arg Phe Ala Glu Leu Val Glu Lys Leu Gly Asp Leu Leu
1145             1150                 1155

Gln Ala Asn Val Gln Gln Asp Gly Lys Asp Tyr Ile Pro Ile Asn
1160             1165                 1170

Ala Ile Leu Thr Gly Asn Ser Gly Phe Thr Tyr Ser Thr Pro Ala
1175             1180                 1185

Phe Ser Glu Asp Phe Phe Lys Glu Ser Ile Ser Ala Pro Lys Phe
1190             1195                 1200

Asn Ser Gly Ser Ser Asp Asp Val Arg Tyr Val Asn Ala Phe Lys
1205             1210                 1215

Phe Met Ser Leu Glu Arg Ile Lys Thr Phe Glu Glu Leu Leu Pro
1220             1225                 1230

Asn Ala Thr Ser Met Phe Asp Asp Tyr Gln Gly Asp Ser Ser Thr
1235             1240                 1245

Leu Leu Ala Ser Pro Met Leu Lys Arg Phe Thr Trp Thr Asp Ser
1250             1255                 1260

Lys Pro Lys Ala Ser Leu Lys Ile Asp Leu Arg Val Thr Ser Lys
1265             1270                 1275

Ser Lys Glu Ser Gly Leu Ser Asp Val Ser Arg Pro Ser Phe Cys
1280             1285                 1290

His Ser Ser Cys Gly His Val Ser Glu Gly Lys Arg Arg Phe Thr
1295             1300                 1305

Tyr Asp His Ala Glu Leu Glu Arg Lys Ile Ala Cys Cys Ser Pro
1310             1315                 1320

Pro Pro Asp Tyr Asn Ser Val Val Leu Tyr Ser Thr Pro Pro Ile
1325             1330                 1335

<210> SEQ ID NO 16
<211> LENGTH: 5830
<212> TYPE: DNA
<213> ORGANISM: Homo sapiens

<400> SEQUENCE: 16
actgagtccc gggaccccgg gagagcggtc agtgtgtggt cgctgcgttt cctctgcctg     60
cgccgggcat cacttgcgcg ccgcagaaag tccgtctggc agcctggata tcctctccta    120
ccggcacccg cagacgcccc tgcagccgcc ggtcggcgcc cgggctccct agccctgtgc    180

-continued

```
gctcaactgt cctgcgctgc ggggtgccgc gagttccacc tccgcgcctc cttctctaga    240
caggcgctgg gagaaagaac cggctcccga gttctgggca tttcgcccgg ctcgaggtgc    300
aggatgcaga gcaaggtgct gctggccgtc gccctgtggc tctgcgtgga gacccgggcc    360
gcctctgtgg gtttgcctag tgtttctctt gatctgccca ggctcagcat acaaaaagac    420
atacttacaa ttaaggctaa tacaactctt caaattactt gcaggggaca gagggacttg    480
gactggcttt ggcccaataa tcagagtggc agtgagcaaa gggtggaggt gactgagtgc    540
agcgatggcc tcttctgtaa gacactcaca attccaaaag tgatcggaaa tgacactgga    600
gcctacaagt gcttctaccg ggaaactgac ttggcctcgg tcatttatgt ctatgttcaa    660
gattacagat ctccatttat tgcttctgtt agtgaccaac atggagtcgt gtacattact    720
gagaacaaaa acaaaactgt ggtgattcca tgtctcgggt ccatttcaaa tctcaacgtg    780
tcactttgtg caagataccc agaaaagaga tttgttcctg atggtaacag aatttcctgg    840
gacagcaaga agggctttac tattcccagc tacatgatca gctatgctgg catggtcttc    900
tgtgaagcaa aaattaatga tgaaagttac cagtctatta tgtacatagt tgtcgttgta    960
gggtatagga tttatgatgt ggttctgagt ccgtctcatg aattgaact atctgttgga    1020 gaaaagcttg tcttaaattg tacagcaaga actgaactaa atgtggggat tgacttcaac    1080
tgggaatacc cttcttcgaa gcatcagcat aagaaacttg taaaccgaga cctaaaaacc    1140
cagtctggga gtgagatgaa gaaattttg agcaccttaa ctatagatgg tgtaacccgg    1200
agtgaccaag gattgtacac ctgtgcagca tccagtgggc tgatgaccaa gaagaacagc    1260
acatttgtca gggtccatga aaaacctttt gttgcttttg gaagtggcat ggaatctctg    1320
gtggaagcca cggtgggga gcgtgtcaga atccctgcga agtaccttgg ttacccaccc    1380
ccagaaataa aatggtataa aaatggaata ccccttgagt ccaatcacac aattaaagcg    1440
gggcatgtac tgacgattat ggaagtgagt gaaagagaca caggaaaatta cactgtcatc    1500 cttaccaatc ccatttcaaa ggagaagcag agccatgtgg tctctctggt tgtgtatgtc    1560
ccaccccaga ttggtgagaa atctctaatc tctcctgtgg attcctacca gtacggcacc    1620
actcaaacgc tgacatgtac ggtctatgcc attcctcccc gcatcacat ccactggtat    1680 tggcagttgg aggaagagtg cgccaacgag cccagccaag ctgtctcagt gacaaaccca    1740
tacccttgtg aagaatggag aagtgtggag gacttccagg gaggaaataa aattgaagtt    1800
aataaaaatc aatttgctct aattgaagga aaaacaaaa ctgtaagtac ccttgttatc    1860
caagcggcaa atgtgtcagc tttgtacaaa tgtgaagcgg tcaacaaagt cgggagagga    1920
gagagggtga tctccttcca cgtgaccagg ggtcctgaaa ttactttgca acctgacatg    1980
cagcccactg agcaggagag cgtgtctttg tggtgcactg cagacagatc tacgtttgag    2040
aacctcacat ggtacaagct tggcccacag cctctgccaa tccatgtggg agagttgccc    2100
acacctgttt gcaagaactt ggatactctt tggaaattga atgccaccat gttctctaat    2160
agcacaaatg acatttgat catggagctt aagaatgcat ccttgcagga ccaaggagac    2220
tatgtctgcc ttgctcaaga caggaagacc aagaaaagac attgcgtggt caggcagctc    2280
acagtcctag agcgtgtggc acccacgatc acaggaaacc tggagaatca gacgacaagt    2340
attggggaaa gcatcgaagt ctcatgcacg gcatctggga atccccctcc acagatcatg    2400
tggtttaaag ataatgagac ccttgtagaa gactcaggca ttgtattgaa ggatgggaac    2460
cggaacctca ctatccgcag agtgaggaag gaggacgaag gcctctacac ctgccaggca    2520
tgcagtgttc ttggctgtgc aaaagtggag gcatttttca taatagaagg tgcccaggaa    2580
```

```
aagacgaact tggaaatcat tattctagta ggcacggcgg tgattgccat gttcttctgg    2640
ctacttcttg tcatcatcct acggaccgtt aagcgggcca atggagggga actgaagaca    2700
ggctacttgt ccatcgtcat ggatccagat gaactcccat ggatgaaca ttgtgaacga    2760
ctgccttatg atgccagcaa atgggaattc cccagagacc ggctgaagct aggtaagcct    2820
cttggccgtg gtgcctttgg ccaagtgatt gaagcagatg cctttggaat tgacaagaca    2880
gcaacttgca ggacagtagc agtcaaaatg ttgaaagaag gagcaacaca cagtgagcat    2940
cgagctctca tgtctgaact caagatcctc attcatattg gtcaccatct caatgtggtc    3000
aaccttctag gtgcctgtac caagccagga gggccactca tggtgattgt ggaattctgc    3060
aaatttggaa acctgtccac ttacctgagg agcaagagaa atgaatttgt ccctacaag    3120
accaaagggg cacgattccg tcaagggaaa gactacgttg gagcaatccc tgtggatctg    3180
aaacggcgct tggacagcat caccagtagc cagagctcag ccagctctgg atttgtggag    3240
gagaagtccc tcagtgatgt agaagaagag gaagctcctg aagatctgta taaggacttc    3300
ctgaccttgg agcatctcat ctgttacagc ttccaagtgg ctaagggcat ggagttcttg    3360
gcatcgcgaa agtgtatcca cagggacctg gcggcacgaa atatcctctt atcggagaag    3420
aacgtggtta aaatctgtga ctttggcttg gcccgggata tttataaaga tccagattat    3480
gtcagaaaag gagatgctcg cctcccttgg aaatggatgg ccccagaaac aattttgac    3540
agagtgtaca caatccagag tgacgtctgg tcttttggtg ttttgctgtg ggaaatattt    3600
tccttaggtg cttctccata tcctggggta aagattgatg aagaattgt taggcgattg    3660
aaagaaggaa ctagaatgag ggcccctgat tatactacac cagaaatgta ccagaccatg    3720
ctggactgct ggcacgggga gcccagtcag agacccacgt tttcagagtt ggtgaacat    3780
ttgggaaatc tcttgcaagc taatgctcag caggatggca aagactacat tgttcttccg    3840
atatcagaga ctttgagcat ggaagaggat tctggactct ctctgcctac ctcacctgtt    3900
tcctgtatgg aggaggagga agtatgtgac cccaaattcc attatgacaa cacagcagga    3960
atcagtcagt atctgcagaa cagtaagcga aagagccggc ctgtgagtgt aaaaacattt    4020
gaagatatcc cgttagaaga accagaagta aaagtaatcc cagatgacaa ccagacggac    4080
agtggtatgg ttcttgcctc agaagagctg aaaactttgg aagacagaac caattatct    4140
ccatcttttg gtggaatggt gcccagcaaa gcagggagt ctgtggcatc tgaaggctca    4200
aaccagacaa gcggctacca gtccggatat cactccgatg acacagacac caccgtgtac    4260
tccagtgagg aagcagaact tttaaagctg atagagattg gagtgcaaac cggtagcaca    4320
gcccagattc tccagcctga ctcggggacc acactgagct ctcctcctgt taaaaggaa    4380
gcatccacac cccaactccc ggacatcaca tgagaggtct gctcagattt tgaagtgttg    4440
ttcttttccac cagcaggaag tagccgcatt tgattttcat ttcgacaaca gaaaaaggac    4500
ctcggactgc agggagccag tcttctaggc atatcctgga agaggcttgt gacccaagaa    4560
tgtgtctgtg tcttctccca gtgttgacct gatcctcttt tttcattcat ttaaaaagca    4620
ttatcatgcc cctgctgcgg gtctcaccat gggtttagaa caaagagctt caagcaatgg    4680
ccccatcctc aaagaagtag cagtacctgg ggagctgaca cttctgtaaa actagaagat    4740
aaaccaggca acgtaagtgt tcgaggtgtt gaagatggga aggatttgca gggctgagtc    4800
tatccaagag gctttgttta ggacgtgggt cccaagccaa gccttaagtg tggaattcgg    4860
attgatagaa aggaagacta acgttacctt gctttggaga gtactggagc ctgcaaatgc    4920
attgtgtttg ctctggtgga ggtgggcatg gggtctgttc tgaaatgtaa agggttcaga    4980
```

-continued

```
cggggtttct ggttttagaa ggttgcgtgt tcttcgagtt gggctaaagt agagttcgtt      5040
gtgctgtttc tgactcctaa tgagagttcc ttccagaccg ttagctgtct ccttgccaag      5100
ccccaggaag aaaatgatgc agctctggct ccttgtctcc caggctgatc ctttattcag      5160
aataccacaa agaaaggaca ttcagctcaa ggctccctgc cgtgttgaag agttctgact      5220
gcacaaacca gcttctggtt tcttctggaa tgaataccct catatctgtc ctgatgtgat      5280
atgtctgaga ctgaatgcgg gaggttcaat gtgaagctgt gtgtggtgtc aaagtttcag      5340
gaaggatttt acccttttgt tcttcccccct gtccccaacc cactctcacc ccgcaaccca     5400
tcagtatttt agttatttgg cctctactcc agtaaacctg attgggtttg ttcactctct      5460
gaatgattat tagccagact tcaaaattat tttatagccc aaattataac atctattgta      5520
ttatttagac ttttaacata tagagctatt tctactgatt tttgcccttg ttctgtcctt      5580
tttttcaaaa aagaaaatgt gttttttgtt tggtaccata gtgtgaaatg ctgggaacaa      5640
tgactataag acatgctatg gcacatatat ttatagtctg tttatgtaga aacaaatgta      5700
atatattaaa gccttatata taatgaactt tgtactattc acattttgta tcagtattat      5760
gtagcataac aaaggtcata atgctttcag caattgatgt cattttatta aagaacattg      5820
aaaaacttga                                                            5830
```

<210> SEQ ID NO 17
<211> LENGTH: 1356
<212> TYPE: PRT
<213> ORGANISM: Homo sapiens

<400> SEQUENCE: 17

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220
```

-continued

```
Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
            245                 250                 255

Asp Phe Asn Trp Glu Tyr Pro Ser Ser Lys His Gln His Lys Lys Leu
        260                 265                 270

Val Asn Arg Asp Leu Lys Thr Gln Ser Gly Ser Glu Met Lys Lys Phe
    275                 280                 285

Leu Ser Thr Leu Thr Ile Asp Gly Val Thr Arg Ser Asp Gln Gly Leu
290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655
```

-continued

Arg Gln Leu Thr Val Leu Glu Arg Val Ala Pro Thr Ile Thr Gly Asn
            660                 665                 670
Leu Glu Asn Gln Thr Thr Ser Ile Gly Glu Ser Ile Glu Val Ser Cys
        675                 680                 685
Thr Ala Ser Gly Asn Pro Pro Pro Gln Ile Met Trp Phe Lys Asp Asn
690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                725                 730                 735
Cys Gln Ala Cys Ser Val Leu Gly Cys Ala Lys Val Glu Ala Phe Phe
            740                 745                 750
Ile Ile Glu Gly Ala Gln Glu Lys Thr Asn Leu Glu Ile Ile Ile Leu
        755                 760                 765
Val Gly Thr Ala Val Ile Ala Met Phe Phe Trp Leu Leu Leu Val Ile
    770                 775                 780
Ile Leu Arg Thr Val Lys Arg Ala Asn Gly Gly Glu Leu Lys Thr Gly
785                 790                 795                 800
Tyr Leu Ser Ile Val Met Asp Pro Asp Glu Leu Pro Leu Asp Glu His
                805                 810                 815
Cys Glu Arg Leu Pro Tyr Asp Ala Ser Lys Trp Glu Phe Pro Arg Asp
            820                 825                 830
Arg Leu Lys Leu Gly Lys Pro Leu Gly Arg Gly Ala Phe Gly Gln Val
        835                 840                 845
Ile Glu Ala Asp Ala Phe Gly Ile Asp Lys Thr Ala Thr Cys Arg Thr
    850                 855                 860
Val Ala Val Lys Met Leu Lys Glu Gly Ala Thr His Ser Glu His Arg
865                 870                 875                 880
Ala Leu Met Ser Glu Leu Lys Ile Leu Ile His Ile Gly His His Leu
                885                 890                 895
Asn Val Val Asn Leu Leu Gly Ala Cys Thr Lys Pro Gly Gly Pro Leu
            900                 905                 910
Met Val Ile Val Glu Phe Cys Lys Phe Gly Asn Leu Ser Thr Tyr Leu
        915                 920                 925
Arg Ser Lys Arg Asn Glu Phe Val Pro Tyr Lys Thr Lys Gly Ala Arg
    930                 935                 940
Phe Arg Gln Gly Lys Asp Tyr Val Gly Ala Ile Pro Val Asp Leu Lys
945                 950                 955                 960
Arg Arg Leu Asp Ser Ile Thr Ser Ser Gln Ser Ser Ala Ser Ser Gly
                965                 970                 975
Phe Val Glu Glu Lys Ser Leu Ser Asp Val Glu Glu Glu Glu Ala Pro
            980                 985                 990
Glu Asp Leu Tyr Lys Asp Phe Leu Thr Leu Glu His Leu Ile Cys Tyr
        995                 1000                1005
Ser Phe Gln Val Ala Lys Gly Met Glu Phe Leu Ala Ser Arg Lys
    1010                1015                1020
Cys Ile His Arg Asp Leu Ala Ala Arg Asn Ile Leu Leu Ser Glu
    1025                1030                1035
Lys Asn Val Val Lys Ile Cys Asp Phe Gly Leu Ala Arg Asp Ile
    1040                1045                1050
Tyr Lys Asp Pro Asp Tyr Val Arg Lys Gly Asp Ala Arg Leu Pro
    1055                1060                1065
Leu Lys Trp Met Ala Pro Glu Thr Ile Phe Asp Arg Val Tyr Thr
    1070                1075                1080

-continued

| | | | | | | | | | | |
|---|---|---|---|---|---|---|---|---|---|---|
| Ile | Gln | Ser | Asp | Val | Trp | Ser | Phe | Gly | Val | Leu | Leu | Trp | Glu | Ile |
| 1085 | | | | 1090 | | | | | 1095 | | | | | |
| Phe | Ser | Leu | Gly | Ala | Ser | Pro | Tyr | Pro | Gly | Val | Lys | Ile | Asp | Glu |
| 1100 | | | | | 1105 | | | | | 1110 | | | | |
| Glu | Phe | Cys | Arg | Arg | Leu | Lys | Glu | Gly | Thr | Arg | Met | Arg | Ala | Pro |
| 1115 | | | | | 1120 | | | | | 1125 | | | | |
| Asp | Tyr | Thr | Thr | Pro | Glu | Met | Tyr | Gln | Thr | Met | Leu | Asp | Cys | Trp |
| 1130 | | | | | 1135 | | | | | 1140 | | | | |
| His | Gly | Glu | Pro | Ser | Gln | Arg | Pro | Thr | Phe | Ser | Glu | Leu | Val | Glu |
| 1145 | | | | | 1150 | | | | | 1155 | | | | |
| His | Leu | Gly | Asn | Leu | Leu | Gln | Ala | Asn | Ala | Gln | Gln | Asp | Gly | Lys |
| 1160 | | | | | 1165 | | | | | 1170 | | | | |
| Asp | Tyr | Ile | Val | Leu | Pro | Ile | Ser | Glu | Thr | Leu | Ser | Met | Glu | Glu |
| 1175 | | | | | 1180 | | | | | 1185 | | | | |
| Asp | Ser | Gly | Leu | Ser | Leu | Pro | Thr | Ser | Pro | Val | Ser | Cys | Met | Glu |
| 1190 | | | | | 1195 | | | | | 1200 | | | | |
| Glu | Glu | Glu | Val | Cys | Asp | Pro | Lys | Phe | His | Tyr | Asp | Asn | Thr | Ala |
| 1205 | | | | | 1210 | | | | | 1215 | | | | |
| Gly | Ile | Ser | Gln | Tyr | Leu | Gln | Asn | Ser | Lys | Arg | Lys | Ser | Arg | Pro |
| 1220 | | | | | 1225 | | | | | 1230 | | | | |
| Val | Ser | Val | Lys | Thr | Phe | Glu | Asp | Ile | Pro | Leu | Glu | Glu | Pro | Glu |
| 1235 | | | | | 1240 | | | | | 1245 | | | | |
| Val | Lys | Val | Ile | Pro | Asp | Asp | Asn | Gln | Thr | Asp | Ser | Gly | Met | Val |
| 1250 | | | | | 1255 | | | | | 1260 | | | | |
| Leu | Ala | Ser | Glu | Glu | Leu | Lys | Thr | Leu | Glu | Asp | Arg | Thr | Lys | Leu |
| 1265 | | | | | 1270 | | | | | 1275 | | | | |
| Ser | Pro | Ser | Phe | Gly | Gly | Met | Val | Pro | Ser | Lys | Ser | Arg | Glu | Ser |
| 1280 | | | | | 1285 | | | | | 1290 | | | | |
| Val | Ala | Ser | Glu | Gly | Ser | Asn | Gln | Thr | Ser | Gly | Tyr | Gln | Ser | Gly |
| 1295 | | | | | 1300 | | | | | 1305 | | | | |
| Tyr | His | Ser | Asp | Asp | Thr | Asp | Thr | Thr | Val | Tyr | Ser | Ser | Glu | Glu |
| 1310 | | | | | 1315 | | | | | 1320 | | | | |
| Ala | Glu | Leu | Leu | Lys | Leu | Ile | Glu | Ile | Gly | Val | Gln | Thr | Gly | Ser |
| 1325 | | | | | 1330 | | | | | 1335 | | | | |
| Thr | Ala | Gln | Ile | Leu | Gln | Pro | Asp | Ser | Gly | Thr | Thr | Leu | Ser | Ser |
| 1340 | | | | | 1345 | | | | | 1350 | | | | |
| Pro | Pro | Val | | | | | | | | | | | | |
| 1355 | | | | | | | | | | | | | | |

<210> SEQ ID NO 18
<211> LENGTH: 675
<212> TYPE: DNA
<213> ORGANISM: Artificial Sequence
<220> FEATURE:
<223> OTHER INFORMATION: Recombinant fusion protein or sequence encoding same

<400> SEQUENCE: 18

```
atggtcagct actgggacac cggggtcctg ctgtgcgcgc tgctcagctg tctgcttctc      60
acaggatctg gtagaccttt cgtagagatg tacagtgaaa tccccgaaat tatacacatg     120
actgaaggaa gggagctcgt cattccctgc cgggttacgt cacctaacat cactgttact     180
ttaaaaaagt ttccacttga cactttgatc cctgatggaa aacgcataat ctgggacagt     240
agaaagggct tcatcatatc aaatgcaacg tacaaagaaa tagggcttct gacctgtgaa     300
gcaacagtca atgggcattt gtataagaca aactatctca cacatcgaca aacccagccc     360
```

```
cgagaaccac aggtgtacac cctgcccca tcccgggatg agctgaccaa gaaccaggtc      420
agcctgacct gcctggtcaa aggcttctat cccagcgaca tcgccgtgga gtgggagagc      480
aatgggcagc cggagaacaa ctacaagacc acgcctcccg tgctggactc cgacggctcc      540
ttcttcctct acagcaagct caccgtggac aagagcaggt ggcagcaggg gaacgtcttc      600
tcatgctccg tgatgcatga ggctctgcac aaccactaca cgcagaagag cctctccctg      660
tctccgggta aatag                                                      675

<210> SEQ ID NO 19
<211> LENGTH: 224
<212> TYPE: PRT
<213> ORGANISM: Artificial Sequence
<220> FEATURE:
<223> OTHER INFORMATION: Recombinant fusion protein or sequence encoding
      same

<400> SEQUENCE: 19

Met Val Ser Tyr Trp Asp Thr Gly Val Leu Leu Cys Ala Leu Leu Ser
1               5                   10                  15

Cys Leu Leu Leu Thr Gly Ser Gly Arg Pro Phe Val Glu Met Tyr Ser
            20                  25                  30

Glu Ile Pro Glu Ile Ile His Met Thr Glu Gly Arg Glu Leu Val Ile
        35                  40                  45

Pro Cys Arg Val Thr Ser Pro Asn Ile Thr Val Thr Leu Lys Lys Phe
    50                  55                  60

Pro Leu Asp Thr Leu Ile Pro Asp Gly Lys Arg Ile Ile Trp Asp Ser
65                  70                  75                  80

Arg Lys Gly Phe Ile Ile Ser Asn Ala Thr Tyr Lys Glu Ile Gly Leu
                85                  90                  95

Leu Thr Cys Glu Ala Thr Val Asn Gly His Leu Tyr Lys Thr Asn Tyr
            100                 105                 110

Leu Thr His Arg Gln Thr Gln Pro Arg Glu Pro Gln Val Tyr Thr Leu
        115                 120                 125

Pro Pro Ser Arg Asp Glu Leu Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 20
<211> LENGTH: 717
<212> TYPE: DNA
<213> ORGANISM: Artificial Sequence
<220> FEATURE:
<223> OTHER INFORMATION: Recombinant fusion protein or sequence encoding
      same

<400> SEQUENCE: 20
atggtcagct actgggacac cggggtcctg ctgtgcgcgc tgctcagctg tctgcttctc      60
acaggatctg gtagaccttt cgtagagatg tacagtgaaa tccccgaaat tatacacatg      120
```

-continued

```
actgaaggaa gggagctcgt cattccctgc cgggttacgt cacctaacat cactgttact    180
ttaaaaaagt ttccacttga cactttgatc cctgatggaa aacgcataat ctgggacagt    240
agaaagggct tcatcatatc aaatgcaacg tacaaagaaa tagggcttct gacctgtgaa    300
gcaacagtca atgggcattt gtataagaca aactatctca cacatcgaca aaccccttcc    360
tgtgtgcccc tgatgcgatg cgggggctgc tgcaatcagc cccgagaacc acaggtgtac    420
accctgcccc catcccggga tgagctgacc aagaaccagg tcagcctgac ctgcctggtc    480
aaaggcttct atcccagcga catcgccgtg gagtgggaga gcaatgggca gccggagaac    540
aactacaaga ccacgcctcc cgtgctggac tccgacggct ccttcttcct ctacagcaag    600
ctcaccgtgg acaagagcag gtggcagcag gggaacgtct tctcatgctc cgtgatgcat    660
gaggctctgc acaaccacta cacgcagaag agcctctccc tgtctccggg taaatag      717
```

<210> SEQ ID NO 21
<211> LENGTH: 238
<212> TYPE: PRT
<213> ORGANISM: Artificial Sequence
<220> FEATURE:
<223> OTHER INFORMATION: Recombinant fusion protein or sequence encoding same

<400> SEQUENCE: 21

```
Met Val Ser Tyr Trp Asp Thr Gly Val Leu Leu Cys Ala Leu Leu Ser
1               5                   10                  15
Cys Leu Leu Leu Thr Gly Ser Gly Arg Pro Phe Val Glu Met Tyr Ser
            20                  25                  30
Glu Ile Pro Glu Ile Ile His Met Thr Glu Gly Arg Glu Leu Val Ile
        35                  40                  45
Pro Cys Arg Val Thr Ser Pro Asn Ile Thr Val Thr Leu Lys Lys Phe
    50                  55                  60
Pro Leu Asp Thr Leu Ile Pro Asp Gly Lys Arg Ile Ile Trp Asp Ser
65                  70                  75                  80
Arg Lys Gly Phe Ile Ile Ser Asn Ala Thr Tyr Lys Glu Ile Gly Leu
                85                  90                  95
Leu Thr Cys Glu Ala Thr Val Asn Gly His Leu Tyr Lys Thr Asn Tyr
            100                 105                 110
Leu Thr His Arg Gln Thr Pro Ser Cys Val Pro Leu Met Arg Cys Gly
        115                 120                 125
Gly Cys Cys Asn Gln Pro Arg Glu Pro Gln Val Tyr Thr Leu Pro Pro
    130                 135                 140
Ser Arg Asp Glu Leu Thr Lys Asn Gln Val Ser Leu Thr Cys Leu Val
145                 150                 155                 160
Lys Gly Phe Tyr Pro Ser Asp Ile Ala Val Glu Trp Glu Ser Asn Gly
                165                 170                 175
Gln Pro Glu Asn Asn Tyr Lys Thr Thr Pro Pro Val Leu Asp Ser Asp
            180                 185                 190
Gly Ser Phe Phe Leu Tyr Ser Lys Leu Thr Val Asp Lys Ser Arg Trp
        195                 200                 205
Gln Gln Gly Asn Val Phe Ser Cys Ser Val Met His Glu Ala Leu His
    210                 215                 220
Asn His Tyr Thr Gln Lys Ser Leu Ser Leu Ser Pro Gly Lys
225                 230                 235
```

```
<210> SEQ ID NO 22
<211> LENGTH: 702
<212> TYPE: DNA
<213> ORGANISM: Artificial Sequence
<220> FEATURE:
<223> OTHER INFORMATION: Recombinant fusion protein or sequence encoding
      same

<400> SEQUENCE: 22
atggtcagct actgggacac cggggtcctg ctgtgcgcgc tgctcagctg tctgcttctc      60
acaggatctg gtagacettt cgtagagatg tacagtgaaa tccccgaaat tatacacatg     120
actgaaggaa gggagctcgt cattccctgc cgggttacgt cacctaacat cactgttact     180
ttaaaaaagt ttccacttga cactttgatc cctgatggaa aacgcataat ctgggacagt     240
agaaagggct tcatcatatc aaatgcaacg tacaaagaaa tagggcttct gacctgtgaa     300
gcaacagtca atgggcattt gtataagaca aactatctca cacatcgaca aaccggtgga     360
ggtggaggtg gaggtggagg tcagccccga gaaccacagg tgtacaccct gcccccatcc     420
cgggatgagc tgaccaagaa ccaggtcagc ctgacctgcc tggtcaaagg cttctatccc     480
agcgacatcg ccgtggagtg ggagagcaat gggcagccgg agaacaacta caagaccacg     540
cctcccgtgc tggactccga cggctccttc ttcctctaca gcaagctcac cgtggacaag     600
agcaggtggc agcaggggaa cgtcttctca tgctccgtga tgcatgaggc tctgcacaac     660
cactacacgc agaagagcct ctccctgtct ccgggtaaat ag                        702

<210> SEQ ID NO 23
<211> LENGTH: 233
<212> TYPE: PRT
<213> ORGANISM: Artificial Sequence
<220> FEATURE:
<223> OTHER INFORMATION: Recombinant fusion protein or sequence encoding
      same

<400> SEQUENCE: 23

Met Val Ser Tyr Trp Asp Thr Gly Val Leu Leu Cys Ala Leu Leu Ser
1               5                   10                  15

Cys Leu Leu Leu Thr Gly Ser Gly Arg Pro Phe Val Glu Met Tyr Ser
            20                  25                  30

Glu Ile Pro Glu Ile Ile His Met Thr Glu Gly Arg Glu Leu Val Ile
        35                  40                  45

Pro Cys Arg Val Thr Ser Pro Asn Ile Thr Val Thr Leu Lys Lys Phe
    50                  55                  60

Pro Leu Asp Thr Leu Ile Pro Asp Gly Lys Arg Ile Ile Trp Asp Ser
65                  70                  75                  80

Arg Lys Gly Phe Ile Ile Ser Asn Ala Thr Tyr Lys Glu Ile Gly Leu
                85                  90                  95

Leu Thr Cys Glu Ala Thr Val Asn Gly His Leu Tyr Lys Thr Asn Tyr
            100                 105                 110

Leu Thr His Arg Gln Thr Gly Gly Gly Gly Gly Gly Gly Gly Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190
```

Tyr Ser Lys Leu Thr Val Asp Lys Ser Arg Trp Gln Gln Gly Asn Val
    195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 24
<211> LENGTH: 1095
<212> TYPE: DNA
<213> ORGANISM: Artificial Sequence
<220> FEATURE:
<223> OTHER INFORMATION: Recombinant fusion protein or sequence encoding
      same

<400> SEQUENCE: 24
atggtcagct actgggacac cggggtcctg ctgtgcgcgc tgctcagctg tctgcttctc      60
acaggatctg gtagaccttt cgtagagatg tacagtgaaa tccccgaaat tatacacatg     120
actgaaggaa gggagctcgt cattccctgc cgggttacgt cacctaacat cactgttact     180
ttaaaaaagt ttccacttga cactttgatc cctgatggaa aacgcataat ctgggacagt     240
agaaagggct tcatcatatc aaatgcaacg tacaaagaaa tagggcttct gacctgtgaa     300
gcaacagtca atgggcattt gtataagaca aactatctca cacatcgaca aaccggtgga     360
ggtggatcgg gtggaggtgg atcgggtgga ggtggatcgc taagagctg cgacaaaact     420 cacacatgcc caccgtgccc agcacctgaa ctcctggggg gaccgtcagt cttcctcttc     480 ccccaaaac ccaaggacac cctcatgatc tcccggaccc ctgaggtcac atgcgtggtg     540
gtggacgtga gccacgaaga ccctgaggtc aagttcaact ggtacgtgga cggcgtggag     600
gtgcataatg ccaagacaaa gccgcgggag gagcagtaca acagcacgta ccgtgtggtc     660
agcgtcctca ccgtcctgca ccaggactgg ctgaatggca aggagtacaa gtgcaaggtc     720
tccaacaaag ccctcccagc ccccatcgag aaaaccatct ccaaagccaa agggcagccc     780
cgagaaccac aggtgtacac cctgccccca tcccgggatg agctgaccaa gaaccaggtc     840
agcctgacct gcctggtcaa aggcttctat cccagcgaca tcgccgtgga gtgggagagc     900
aatgggcagc cggagaacaa ctacaagacc acgcctcccg tgctggactc cgacggctcc     960
ttcttcctct acagcaagct caccgtggac aagagcaggt ggcagcaggg gaacgtcttc    1020
tcatgctccg tgatgcatga ggctctgcac aaccactaca cgcagaagag cctctccctg    1080
tctccgggta aatag                                                     1095

<210> SEQ ID NO 25
<211> LENGTH: 364
<212> TYPE: PRT
<213> ORGANISM: Artificial Sequence
<220> FEATURE:
<223> OTHER INFORMATION: Recombinant fusion protein or sequence encoding
      same

<400> SEQUENCE: 25

Met Val Ser Tyr Trp Asp Thr Gly Val Leu Leu Cys Ala Leu Leu Ser
1               5                   10                  15

Cys Leu Leu Leu Thr Gly Ser Gly Arg Pro Phe Val Glu Met Tyr Ser
            20                  25                  30

Glu Ile Pro Glu Ile Ile His Met Thr Glu Gly Arg Glu Leu Val Ile
        35                  40                  45

Pro Cys Arg Val Thr Ser Pro Asn Ile Thr Val Thr Leu Lys Lys Phe
    50                  55                  60

```
Pro Leu Asp Thr Leu Ile Pro Asp Gly Lys Arg Ile Trp Asp Ser
 65                  70                  75                  80

Arg Lys Gly Phe Ile Ile Ser Asn Ala Thr Tyr Lys Glu Ile Gly Leu
             85                  90                  95

Leu Thr Cys Glu Ala Thr Val Asn Gly His Leu Tyr Lys Thr Asn Tyr
            100                 105                 110

Leu Thr His Arg Gln Thr Gly Gly Gly Ser Gly Gly Gly Gly Ser
            115                 120                 125

Gly Gly Gly Gly Ser Pro Lys Ser Cys Asp Lys Thr His Thr Cys Pro
130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
            355                 360

<210> SEQ ID NO 26
<211> LENGTH: 9
<212> TYPE: PRT
<213> ORGANISM: Artificial Sequence
<220> FEATURE:
<223> OTHER INFORMATION: linker of fusion protein

<400> SEQUENCE: 26

Gly Asp Leu Ile Tyr Arg Asn Gln Lys
1               5

<210> SEQ ID NO 27
<211> LENGTH: 9
<212> TYPE: PRT
<213> ORGANISM: Artificial Sequence
<220> FEATURE:
<223> OTHER INFORMATION: linker moiety for fusion proteins
```

```
<400> SEQUENCE: 27

Gly Gly Gly Gly Gly Gly Gly Gly Gly
1               5

<210> SEQ ID NO 28
<211> LENGTH: 9
<212> TYPE: PRT
<213> ORGANISM: Artificial Sequence
<220> FEATURE:
<223> OTHER INFORMATION: linker moiety for fusion proteins

<400> SEQUENCE: 28

Glu Glu Glu Glu Glu Glu Glu Glu Glu
1               5

<210> SEQ ID NO 29
<211> LENGTH: 9
<212> TYPE: PRT
<213> ORGANISM: Artificial Sequence
<220> FEATURE:
<223> OTHER INFORMATION: linker moiety for fusion proteins

<400> SEQUENCE: 29

Ser Ser Ser Ser Ser Ser Ser Ser Ser
1               5

<210> SEQ ID NO 30
<211> LENGTH: 9
<212> TYPE: PRT
<213> ORGANISM: Artificial Sequence
<220> FEATURE:
<223> OTHER INFORMATION: linker moiety for fusion proteins

<400> SEQUENCE: 30

Gly Gly Gly Gly Gly Cys Pro Pro Cys
1               5

<210> SEQ ID NO 31
<211> LENGTH: 15
<212> TYPE: PRT
<213> ORGANISM: Artificial Sequence
<220> FEATURE:
<223> OTHER INFORMATION: linker moiety for fusion proteins

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 13
<212> TYPE: PRT
<213> ORGANISM: Artificial Sequence
<220> FEATURE:
<223> OTHER INFORMATION: linker moiety for fusion proteins

<400> SEQUENCE: 32

Ser Cys Val Pro Leu Met Arg Cys Gly Gly Cys Cys Asn
1               5                   10

<210> SEQ ID NO 33
<211> LENGTH: 9
<212> TYPE: PRT
<213> ORGANISM: Artificial Sequence
<220> FEATURE:
<223> OTHER INFORMATION: linker moiety for fusion proteins
```

```
<400> SEQUENCE: 33

Gly Asp Leu Ile Tyr Arg Asn Gln Lys
1               5

<210> SEQ ID NO 34
<211> LENGTH: 23
<212> TYPE: PRT
<213> ORGANISM: Artificial Sequence
<220> FEATURE:
<223> OTHER INFORMATION: linker moiety for fusion proteins

<400> SEQUENCE: 34

Gly Gly Gly Gly Gly Gly Gly Gly Pro Ser Cys Val Pro Leu Met
1               5                   10                  15

Arg Cys Gly Gly Cys Cys Asn
            20
```

US 8,658,602 B2

MULTIMERIC CONSTRUCTS

CROSS REFERENCE TO RELATED APPLICATIONS

The present application is a continuation of U.S. Ser. No. 11/716,794, filed Mar. 12, 2007, now U.S. Pat. No. 7,928,072, which is a continuation of PCT/US05/32320, filed Sep. 13, 2005, from which applications priority is claimed under 35 U.S.C. §120, which application claims the benefit under 35 U.S.C. §119(e)(1) to U.S. Provisional Application Ser. Nos. 60/608,887, filed Sep. 13, 2004 and 60/658,209, filed Mar. 4, 2005, all of which applications are incorporated herein by reference in their entireties.

REFERENCE TO SEQUENCE LISTING SUBMITTED VIA EFS-WEB

This application includes a sequence listing in .txt format that is electronically submitted via EFS-Web. The .txt file contains a sequence listing entitled "2013-05-10 0800-0061.01_ST25.txt" created on May 10, 2013 and is 79,776 bytes in size. The sequence listing contained in this .txt file is part of the specification and is hereby incorporated by reference herein in its entirety.

FIELD OF THE INVENTION

The invention relates to recombinantly constructed proteins useful for treating pathological neovascularization, e.g., asthma, arthritis, cancer, and macular degeneration.

BACKGROUND OF THE INVENTION

Pathological neovascularization is a key component of diseases like wet age-related macular degeneration (AMD), proliferative diabetic retinopathy, rheumatoid arthritis, osteoarthritis, and asthma. It also plays an important role in growth and spread of tumors. Neovascularization is regulated by an exquisite balance of pro- and anti-angiogenic factors.

Vascular endothelial growth factor (VEGF) is known to be necessary for neovascularization. Inhibition of VEGF activity has been shown to inhibit neovascularization in animal models of AMD, arthritis and in various tumor models. Methods used to inhibit VEGF activity include antibodies, receptor fusion proteins, peptides and small molecules.

VEGF-R1 (Flt-1) and VEGF-R2 (KDR) proteins have been shown to bind VEGF with high affinity. Both Flt-1 and KDR have seven Ig-like domains in their extracellular region. Domain 2 has been shown to be essential for VEGF binding. Fusions of each of the full-length, soluble receptor (domains 1-7) and domains 1-3 to IgG Fc bind VEGF efficiently. IgG Fc fusions to Ig-like domain 2 alone was, however, incapable of binding VEGF, as was a combination of Ig-like domain 1 and 2. Davis-Smyth, 1996. Therefore, Ig-like domains 1 and 3 seem to be required along with domain 2 for efficient VEGF binding.

BRIEF SUMMARY OF THE INVENTION

According to one embodiment of the invention a fusion protein is provided. The fusion protein has the formula X-Y-Z. X comprises a polypeptide selected from the group consisting of an extracellular receptor, an antibody variable region, a cytokine, a chemokine, and a growth factor. Y consists essentially of a 5-25 amino acid residue polypeptide. Z is a CH3 region of an IgG heavy chain molecule.

Another embodiment of the invention is a polypeptide of the formula X-Y-Z. X comprises a polypeptide selected from the group consisting of an extracellular receptor, an antibody variable region, a cytokine, a chemokine, and a growth factor. Y consists essentially of a linker moiety which provides the spatial separation of 5-25 amino acid residues. Z is a CH3 region of an IgG heavy chain molecule.

Yet another aspect of the invention is a fusion protein of the formula X-Y-Z. X comprises a polypeptide selected from the group consisting of an extracellular receptor, an antibody variable region, a cytokine, a chemokine, and a growth factor. Y consists essentially of a 5-25 amino acid residue polypeptide. Z is an Fc portion of an antibody molecule.

A fusion protein of the formula X-Y-Z is also provided. X comprises a polypeptide selected from the group consisting of an extracellular receptor, an antibody variable region, a cytokine, a chemokine, and a growth factor. Y consists essentially of a linker moiety which provides the spatial separation of 5-25 amino acid residues. Z is an Fc portion of an antibody molecule.

Still another aspect of the invention is a method of multimerizing a polypeptide X. A polypeptide X is linked to a polypeptide Z via a polypeptide Y to form polypeptide XYZ. X comprises a polypeptide selected from the group consisting of an extracellular receptor, an antibody variable region, a cytokine, a chemokine, and a growth factor. Y consists essentially of a 5-25 amino acid residue polypeptide. Z is a CH3 region of an IgG heavy chain molecule. Polypeptide XYZ which is formed multimerizes.

Yet another embodiment of the invention provides a method of multimerizing a polypeptide X. Polypeptide X is linked to a polypeptide Z via a moiety Y to form polymer XYZ. X comprises a polypeptide selected from the group consisting of an extracellular receptor, an antibody variable region, a cytokine, a chemokine, and a growth factor. Y consists essentially of a linker moiety which provides the spatial separation of 5-25 amino acid residues. Z is a CH3 region of an IgG heavy chain molecule. Polypeptide XYZ which is so formed multimerizes.

In one embodiment of the invention a nucleic acid molecule is provided. The nucleic acid molecule encodes a fusion protein which comprises an Ig-like domain 2 of VEGF-R1 (Flt-1); a linker; and a multimerization domain. The fusion protein comprises a sequence selected from the group consisting of SEQ ID NO: 2, 8, 21, 23, and 25.

In another embodiment of the invention a fusion protein is provided. The fusion protein comprises an Ig-like domain 2 of VEGF-R1 (Flt-1), a linker, and a multimerization domain. The fusion protein comprises a sequence selected from the group consisting of SEQ ID NO: 2, 8, 21, 23, and 25.

In another embodiment of the invention an in vitro method is provided. A nucleic acid molecule is delivered to an isolated mammalian cell. The nucleic acid molecule encodes a fusion protein which comprises an Ig-like domain 2 of VEGF-R1 (Flt-1; a linker; and a multimerization domain. The fusion protein comprises a sequence selected from the group consisting of SEQ ID NO: 2, 8, 21, 23, and 25. Expression of the fusion protein is controlled by a promoter. A cell is formed which expresses a fusion protein.

Still another embodiment of the invention is a method for delivering a fusion protein to a mammal. A mammalian cell which expresses the fusion protein is delivered to a mammal. The cell expresses and secretes the fusion protein thereby supplying the fusion protein to the mammal. The fusion protein comprises an Ig-like domain 2 of VEGF-R1 (Flt-1), a linker, and a multimerization domain. The fusion protein comprises a sequence selected from the group consisting of SEQ ID NO: 2, 8, 21, 23, and 25.

Another aspect of the invention is a method for supplying a fusion protein to a mammal. A fusion protein which comprises an Ig-like domain 2 of VEGF-R1 (Flt-1), a linker, and a multimerization domain is delivered to a mammal. The fusion protein comprises a sequence selected from the group consisting of SEQ ID NO: 2, 8, 21, 23, and 25. Alternatively, a nucleic acid construct which encodes said fusion protein can be delivered to the mammal, whereby the fusion protein is expressed by the mammal.

These and other embodiments of the invention which will be described in more detail below provide the art with methods and agents for treating disease related to vascular proliferation and inflammation. The agents may provide increased stability and bioavailability relative to natural forms of the proteins.

BRIEF DESCRIPTION OF THE DRAWINGS

FIG. 13A-13C. FIG. 13A shows expression levels of Flt-1 constructs having various linkers. FIG. 13B shows dimerization or multimerization of Flt-1 constructs having various linkers and a CH3 moiety of Fc of IgG1. The difference between the non-reduced and the reduced conditions indicates that the proteins had multimerized. FIG. 13C shows the inhibitory bioactivity of indicated Flt-1 constructs present in condition medium in a HUVEC proliferation assay in the presence of VEGF. Each of the constructs demonstrated inhibitory activity approaching proliferation levels of the HUVEC in the absence of VEGF.

DETAILED DESCRIPTION OF THE INVENTION

Figure 1:
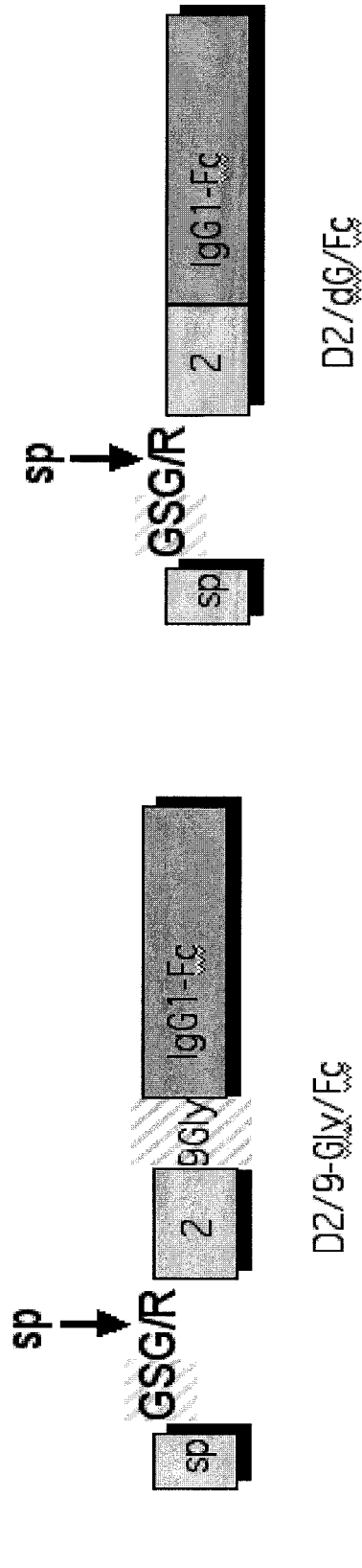
FIG. 1. Flexible region of 9-Gly linker in D2-9Gly-Fc construct. The predicted relative flexibility by Karpus and Schultz (1985) method shows the polyglycine 9-mer (9-Gly) linker (aa 94 to 103) in D2-9Gly-Fc protein as a region with greater flexibility than the average (>1) as compared to D2-Fc construct that does not contain 9-Gly linker. Both fusion proteins contain identical amino acid sequences enclosed in boxes: sp—signal peptide (aa −24 to −1), Flt-1 domain 2 (aa 1 to 93) and IgG1-Fc residues (244 aa). The arrow represents the signal peptidase cleavage site as predicted using the SignalP V2.0 program (Nielsen et al., 1997).
Figure 1:
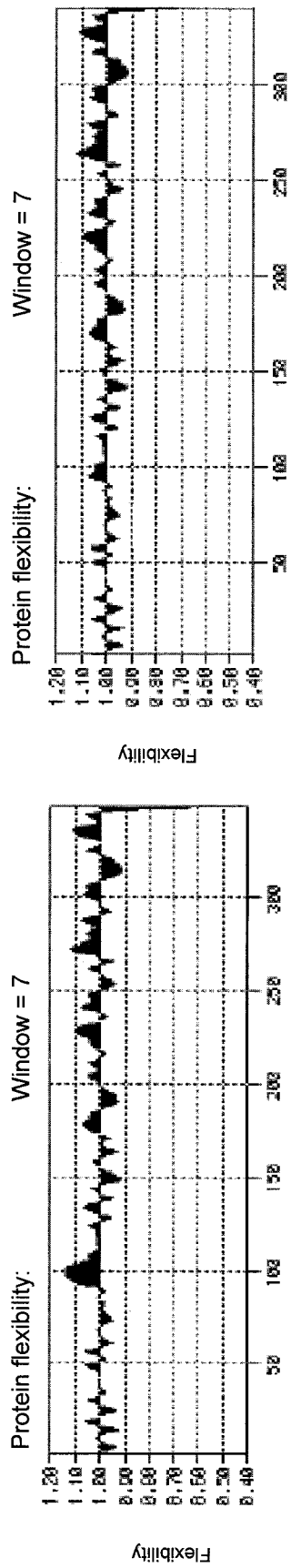

It is a discovery of the present inventors that a Flt-1 Ig-like domain 2 without domains 1 and 3 is capable of efficiently binding VEGF and inhibiting VEGF-dependent endothelial cell proliferation. Domain 2 can be covalently linked to a multimerization domain via a linker. Linkers are typically polypeptide chains. The length of the chain may be 6, 7, 9, 11, 13, 15 or more amino acid residues, but typically is between 5 and 25 residues. Depending upon the length and side chain composition, a linker may have but need not have greater than average flexibility. Flexibility can be calculated using algorithms known in the art. Multimerization domains are those portions of multimeric proteins which promote the association of subunits to form, for example, dimers, trimers, tetramers, etc. Suitable recombinant proteins for efficiently binding VEGF and/or inhibiting VEGF-dependent endothelial cell proliferation are selected from the group consisting of SEQ ID NO: 2, 8, 21, 23, and 25.

1321 Moreover, the inventors have found that the multimerization domains and linkers can be used with a variety of other proteins or portions of proteins to induce multimerization. Such proteins may be those which bind to ligand or receptor only when multimerized, or may be those whose binding affinity is enhanced when multimerized. Suitable proteins for multimerization include extracellular receptors (which include portions thereof), antibody variable regions, cytokines, chemokines, and growth factors. Suitable proteins include tyrosine kinase receptors and senile thereonine kinase receptors. Specific examples of extracellular receptors include EGF-receptor, G protein coupled receptors, FGF receptor, Fc receptors, T cell receptors, etc. Examples of antibody variable regions include Fab, F(ab')2, and ScFv. Examples of cytokines include GM-CSF, IL-1a, IL-113, IL-2, IL-3, IL-4, IL-5, IL-6, IL-7, IL-8, IL-10, IL-12, IL-18, IL-21, IL-23, IFN-a, IFN-13, MIP-1a, MIP-113, TGF-13, TNFa, and TNF-13. Examples of chemokines include BCA-1/BLC, BRAK, Chemokine CC-2, CTACK, CXCL-16, ELC, ENA, ENA-70, ENA-74, ENA-78, Eotaxin, Exodus-2, Fractalkine, GCP-2, GRO, GRO alpha (MGSA), GRO-beta, GRO-gamma, HCC-1, HCC-4, 1-309, IP-10, I-TAC, LAG-1, LD78-beta, LEC/NCC-4, LL-37, Lymphotactin, MCP, MCAF (MCP-1), MCP-2, MCP-3, MCP-4, MDC, MDC, MDC-2, MDC-4, MEC/CCL28, MIG, MIP, MIP-1 alpha, MIP-1 beta, MIP-1 delta, MIP-3/MPIF-1, MIP-3 alpha, MIP-3 bet, MIP-4 (PARC), MIP-5, NAP-2, PARC, PF-4, RANTES, RANTES-2, SDF-1 alpha; SDF-1 beta, TARC, and TECK. Examples of growth factors include Human Amphiregulin, Human Angiogenesis Proteins, Human ACE, Human Angiogenin, Human Angiopoietin, Human Angiostatin, Human Betacellulin, Human BMP, Human BMP-13/CDMP-2, Human BMP-14/CDMP-1, Human BMP-2, Human BMP-3, Human BMP-4, Human BMP-5, Human BMP-6, Human BMP-7, Human BMP-8, Human BMP-9, Human Colony Stimulating Factors, Human flt3-Ligand, Human GCSF, Human GM-CSF, Human M-CSF, Human Connective Tissue Growth Factor, Human Cripto-1, Human Cryptic, Human ECGF, Human EGF, Human EG-VEGF, Human Erythropoietin, Human Fetuin, Human FGF, Human FGF-1, Human FGF10, Human FGF-16, Human FGF-17, Human FGF-18, Human FGF-19, Human FGF2, Human FGF-20, Human FGF-3, Human FGF-4, Human FGF-5, Human FGF-6, Human FGF-7/KGF, Human FGF-8, Human FGF-9, Human FGF-acidic, Human FGF-basic, Human GDF-11, Human GDF-15, Human Growth Hormone Releasing Factor, Human HB-EGF, Human Heregulin, Human fiGF, Human IGF, Human IGF-I, Human IGF-II, Human Inhibin, Human KGF, Human LCGF, Human LIF, Human Miscellaneous Growth Factors, Human MSP, Human Myostatin, Human Myostatin Propeptide, Human Nerve Growth Factor, Human, Oncostatin M, Human PD-ECGF, Human PDGF, Human PDGF (AA Homodimer), Human PDGF (AB Heterodimer), Human PDGF (BB Homodimer), Human PDGF (CC Homodimer), Human PIGF, Human PIGF, Human PIGF-1, Human PIGF-2, Human SCF, Human SMDF, Human Stem Cell Growth Factor, Human SCGF-alpha, Human SCGF-beta, Human Thrombopoietin, Human Transforming Growth Factor, Human TGF-alpha, Human TGF-beta, and Human VEGF.

[331 Flt-1 receptor protein has an extracellular portion which comprises seven Ig-like domains. These are located at residue numbers 32 . . . 123, 151 . . . 214, 230 . . . 327, 335 . . . 421, 428 . . . 553, 556 . . . 654, and 661 . . . 747 of Genbank accession no. P17948, see also SEQ ID NO: 15. Residue numbers 1-26 comprise a signal sequence. Flt-1 protein is encoded by the DNA sequence shown at Genbank accession no. NM_002019 (SEQ ID NO: 14).

Multimerization domains can be used as are known in the art. Sequences of the Fc portion of IgG1 or IgG2 lambda heavy chain can be used, for example, CH3 alone (aa 371-477) or both of CH2 and CH3 domains (aa 247-477). Fc portion of Ig molecules is that which is obtained by cleavage of whole antibody molecules with the enzyme papain. Other means can be used to obtain these portions. For the IgG1 lambda heavy chain protein sequence, see Genbank accession no YI4737 and SEQ ID NO: 10. Other Fc regions can be used for example from other IgG types and from IgA, IgM, IgD, or IgE antibodies. The multimerization region of VEGF can also be used. A DNA sequence encoding VEGF is shown at Genbank accession no. NM003376 and SEQ ID NO: 11. An amino acid sequence of VEGF is shown at Genbank accession no. CAC19513 and SEQ ID NO: 12. The multimerization region of VEGF (SEQ ID NO: 13), encoded by VEGF exon 3 (VEGF Ex3), is at about amino acid residues 7588 of VEGF protein (SEQ ID NO: 12). Multimerization domains will cause at least 5%, 10%, 20%, 30%, 40%, 50%, 60%, 75%, 80%, 85%, 90%, or 95% of the monomeric fusion proteins to migrate on a non-denaturing polyacrylamide gel at a rate appropriate for a multimer. Glycosylation can affect the migration of a protein in a gel. Although particular sequences are shown here, variants such as allelic variants can be used as well. Typically such variants will have at least 85%, 90%, 95%, 97%, 98%, or 99% identity with the disclosed sequence.

Multimerization can be assayed, for example, using reducing and non-reducing gels, as demonstrated herein. Multimerization can also be assayed by detection of increased binding affinity of a protein for its ligand/receptor. BiaCore™ surface plasmon resonance assays can be used in this regard. These assays detect changes in mass by measuring changes in refractive index in an aqueous layer close to a sensor chip surface. Any method known in the art can be used to detect multimerization.

Linker moieties according to the invention can be comprised of for example 5-100 amino acid residues, 5-75 amino acid residues, 5-50 amino acid residues, 5-25 amino acid residues, 5-20 amino acid residues, 5-15 amino acid residues, 5-10 amino acid residues, 5-9 amino acid residues. Examples of useful linkers include: gly9 (SEQ ID NO: 27), glu9 (SEQ ID NO: 28), ser9 (SEQ ID NO: 29), gly5cyspro2cys (SEQ ID NO: 30), (gly4ser)3 (SEQ ID NO: 31), Ser Cys Val Pro Leu Met Arg Cys Gly Gly Cys Cys Asn (SEQ ID NO: 32), Pro Ser Cys Val Pro Leu Met Arg Cys Gly Gly Cys Cys Asn (SEQ ID NO: 13), Gly Asp Leu Ile Tyr Arg Asn Gln Lys (SEQ ID NO: 26), and Gly9ProSerCysValProLeuMetArgCysGlyGlyCys-CysAsn (SEQ ID NO: 34). Other polypeptide linkers which can be used include a polyglycine of different lengths, including of 5, 7, or 30 residues. Additionally, other portions of Flt-1 can be used as a linker, for example domain 3 of Flt-1. See SEQ ID NO: 15. Linker moieties can also be made from other polymers, such as polyethylene glycol. Such linkers can have from 10 to 1000, 10-500, 10-250, 10-100, or 10-50 ethylene glycol monomer units. Suitable polymers should be of a size similar to the size occupied by the appropriate range of amino acid residues. A typical sized polymer would provide a spacing of from about 10-25 angstroms.

Fusion proteins according to the invention can be made by any means known in the art. While such proteins can be made synthetically, or by linking portions which are made, recombinant production can also be used. A fused gene sequence can be produced using the standard tools of recombinant DNA. The fused gene sequence can be inserted into a vector, for example a viral or plasmid vector, for replicating the fused gene sequence. A promoter sequence which is functional in the ultimate recipient cell can be introduced upstream of the fused gene sequence. Promoters used can be constitutive, inducible or repressible. Examples of each type are well-known in the art. The vector can be introduced into a host cell or mammal by any means known in the art. Suitable vectors which can be used include adenovirus, adeno-associated virus, retrovirus, lentivirus, and plasmids. If the vector is in a viral vector and the vector has been packaged, then the virions can be used to infect cells. If naked DNA is used, then transfection or transformation procedures as are appropriate for the particular host cells can be used. Formulations of naked DNA utilizing polymers, liposomes, or nanospheres can be used for fusion gene delivery. Cells which can be transformed or transfected with recombinant constructs according to the invention may be any which are convenient to the artisan. Exemplary cell types which may be used include bacteria, yeast, insects, and mammalian cells. Among mammalian cells, cells of many tissue types may be chosen, as is convenient. Exemplary cells which may be used are fibroblasts, hepatocytes, endothelial cells, stem cells, hematopoietic cells, epithelial cells, myocytes, neuronal cells, and keratinocytes. These cells can be used to produce protein in vitro, or can be delivered to mammals including humans to produce the encoded proteins in vivo. This means of delivery is an alternative to delivering nucleic acid to a mammal; delivering viral vector to a mammal, and delivering fusion protein to a mammal.

Compositions of protein or nucleic acids can be in carriers, such as buffers, aqueous or lipophilic carriers, sterile or non-sterile, pyrogenic or non-pyrogenic vehicles. Non-pyrogenic vehicles are useful for injectible formulations. Formulations can be liquid or solid, for example, lyophilized. Formulations can also be administered as aerosols. Compositions may contain one or more fusion proteins or one or more nucleic acids, or both fusion proteins and nucleic acids. The fusion proteins and or nucleic acids in a composition may be homogeneous, in which case homomultimer proteins will form, or they may be heterogeneous in the composition, in which case heteromultimer proteins will form. In the case of heteromultimers, typically the X moiety will vary between fusion proteins, but the Z moiety will be the same between fusion proteins.

Fusion proteins can be provided to a cell or mammalian host by any means known in the art. Protein can be delivered to the cell or host. Nucleic acid can be administered to the cell or host. Transformed or transfected cells can be administered to the cell or host. In the latter case, cells of the same genetic background are desired to reduce transplantation rejection.

Suitable cells for delivery to mammalian host animals include any mammalian cell type from any organ, tumor, or cell line. For example, human, murine, goat, ovine, bovine, dog, cat, and porcine cells can be used. Suitable cell types for use include without limitation, fibroblasts, hepatocytes, endothelial cells, keratinocytes, hematopoietic cells, epithelial cells, myocytes, neuronal cells, and stem cells.

Means of delivery of fusion proteins or nucleic acids encoding fusion proteins include delivery of cells expressing the fusion proteins, delivery of the fusion proteins, and delivery of nucleic acids encoding the fusion proteins. Fusion proteins, cells, or nucleic acids can be delivered directly to the desired organ or tumor, for example by injection, catheterization, or endoscopy. They can also be delivered intravenously, intrabronchially, intra-tumorally, intrathecally, intramuscularly, intraocularly, topically, subcutaneously, transdermally or per os. Patients who can be effectively treated include those with wet age-related macular degeneration, proliferative diabetic retinopathy, rheumatoid arthritis, osteoarthritis, uveitis, asthma, and cancer. The treatments will improve symptoms and/or markers of disease and/or disease severity.

Nucleic acids can be delivered to mammals, and in particular to humans, in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), adenovirus, AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

Combinations of protein and nucleic acid treatments can be used. For example, a fusion protein according to the invention can be administered to a patient. If a favorable response is observed, then a nucleic acid molecule encoding the fusion protein can be administered for a long term effect. Alternatively, the protein and nucleic acid can be administered simultaneously or approximately simultaneously. In another alternative, an antibody or fusion protein for a ligand can be administered followed by or concomitantly with an antibody or fusion partner for a receptor. Another option employs a combination of nucleic acids in which one encodes an antibody and another encodes a fusion protein. Some antibodies that can be employed in combination with the Flt-1 constructs of the present invention (whether in the protein or nucleic acid form) are bevacizumab and ranibizumab, both directed to VEGF. These are particularly useful for treating cancer and macular degeneration, respectively.

The practice of the present invention employs, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, Second Edition (Sambrook et al., 1989); Current Protocols In Molecular Biology (F. M. Ausubel et al., eds., 1987); Oligonucleotide Synthesis (M. J. Gait, ed., 1984); Animal Cell Culture (R. I. Freshney, ed., 1987); Methods In Enzymology (Academic Press, Inc.); Handbook Of Experimental Immunology (D. M. Wei & C. C. Blackwell, eds.); Gene Transfer Vectors For Mammalian Cells (J. M. Miller & M. P. Calos, eds., 1987); PCR: The Polymerase Chain Reaction, (Mullis et al., eds., 1994); Current Protocols In Immunology (J. E. Coligan et al., eds., 1991); Antibodies: A Laboratory Manual (E. Harlow and D. Lane eds. (1988)); and PCR 2: A Practical Approach (M. J. MacPherson, B. D. Hames and G. R. Taylor eds. (1995)).

A gene delivery vehicle is any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

Gene delivery, gene transfer, and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

The exogenous polynucleotide is inserted into a vector such as adenovirus, partially-deleted adenovirus, fully-deleted adenovirus, adeno-associated virus (AAV), retrovirus, lentivirus, naked plasmid, plasmid/liposome complex, etc. for delivery to the host via intravenous, intramuscular, intraportal or other route of administration. Expression vectors which can be used in the methods and compositions of the present invention include, for example, viral vectors. One of the most frequently used methods of administration of gene therapy, both in vivo and ex vivo, is the use of viral vectors for delivery of the gene. Many species of virus are known, and many have been studied for gene therapy purposes. The most commonly used viral vectors include those derived from adenoviruses, adeno-associated viruses (AAV) and retroviruses, including lentiviruses, such as human immunodeficiency virus (HIV).

Adenovirus is a non-enveloped, nuclear DNA virus with a genome of about 36 kb, which has been well-characterized through studies in classical genetics and molecular biology (Hurwitz, M. S., Adenoviruses Virology, 3rd edition, Fields et al., eds., Raven Press, New York, 1996; Hitt, M. M. et al., Adenovirus Vectors, The Development of Human Gene Therapy, Friedman, T. ed., Cold Spring Harbor Laboratory Press, New York 1999). The viral genes are classified into early (designated E1-E4) and late (designated L1-L5) transcriptional units, referring to the generation of two temporal classes of viral proteins. The demarcation of these events is viral DNA replication. The human adenoviruses are divided into numerous serotypes (approximately 47, numbered accordingly and classified into 6 groups: A, B, C, D, E and F), based upon properties including hemaglutination of red blood cells, oncogenicity, DNA and protein amino acid compositions and homologies, and antigenic relationships.

Recombinant adenoviral vectors have several advantages for use as gene delivery vehicles, including tropism for both dividing and non-dividing cells, minimal pathogenic potential, ability to replicate to high titer for preparation of vector stocks, and the potential to carry large inserts (Berkner, K. L., Curr. Top. Micro. Immunol. 158:39-66, 1992; Jolly, D., Cancer Gene Therapy 1:51-64 1994). Adenoviral vectors with deletions of various adenoviral gene sequences, such as pseudoadenoviral vectors (PAVs) and partially-deleted adenoviral (termed "DeAd"), have been designed to take advantage of the desirable features of adenovirus which render it a suitable vehicle for delivery of nucleic acids to recipient cells.

In particular, pseudoadenoviral vectors (PAVs), also known as 'gutless adenovirus' or mini-adenoviral vectors, are adenoviral vectors derived from the genome of an adenovirus that contain minimal cis-acting nucleotide sequences required for the replication and packaging of the vector genome and which can contain one or more transgenes (See, U.S. Pat. No. 5,882,877 which covers pseudoadenoviral vectors (PAV) and methods for producing PAV, incorporated herein by reference). PAVs have been designed to take advantage of the desirable features of adenovirus which render it a suitable vehicle for gene delivery. While adenoviral vectors can generally carry inserts of up to 8 kb in size by the deletion of regions which are dispensable for viral growth, maximal carrying capacity can be achieved with the use of adenoviral vectors containing deletions of most viral coding sequences, including PAVs. See U.S. Pat. No. 5,882,877 of Gregory et al.; Kochanek et al., Proc. Natl. Acad. Sci. USA 93:5731-5736, 1996; Parks et al., Proc. Natl. Acad. Sci. USA 93:13565-13570, 1996; Lieber et al., J. Virol. 70:8944-8960, 1996; Fisher et al., Virology 217:11-22, 1996; U.S. Pat. No. 5,670,488; PCT Publication No. WO96/33280, published Oct. 24, 1996; PCT Publication No. WO96/40955, published Dec. 19, 1996; PCT Publication No. WO97/25446, published Jul. 19, 1997; PCT Publication No. WO95/29993, published Nov. 9, 1995; PCT Publication No. WO97/00326, published Jan. 3, 1997; Morral et al., Hum. Gene Ther. 10:2709-2716, 1998. Such PAVs, which can accommodate up to about 36 kb of foreign nucleic acid, are advantageous because the carrying capacity of the vector is optimized, while the potential for host immune responses to the vector or the generation of replication-competent viruses is reduced. PAV vectors contain the 5' inverted terminal repeat (ITR) and the 3' ITR nucleotide sequences that contain the origin of replication, and the cis-acting nucleotide sequence required for packaging of the PAV genome, and can accommodate one or more transgenes with appropriate regulatory elements, e.g. promoter, enhancers, etc.

Other, partially deleted adenoviral vectors provide a partially-deleted adenoviral (termed "DeAd") vector in which the majority of adenoviral early genes required for virus replication are deleted from the vector and placed within a producer cell chromosome under the control of a conditional promoter. The deletable adenoviral genes that are placed in the producer cell may include E1A/E1B, E2, E4 (only ORF6 and ORF6/7 need be placed into the cell), pIX and pIVa2. E3 may also be deleted from the vector, but since it is not required for vector production, it can be omitted from the producer cell. The adenoviral late genes, normally under the control of the major late promoter (MLP), are present in the vector, but the MLP may be replaced by a conditional promoter.

Conditional promoters suitable for use in DeAd vectors and producer cell lines include those with the following characteristics: low basal expression in the uninduced state, such that cytotoxic or cytostatic adenovirus genes are not expressed at levels harmful to the cell; and high level expression in the induced state, such that sufficient amounts of viral proteins are produced to support vector replication and assembly. Preferred conditional promoters suitable for use in DeAd vectors and producer cell lines include the dimerizer gene control system, based on the immunosuppressive agents FK506 and rapamycin, the ecdysone gene control systeth and the tetracycline gene control system. Also useful in the present invention may be the GeneSwitch'" technology (Valentis, Inc., Woodlands, Tex.) described in Abruzzese et al., Hum. Gene Ther. 1999 10:1499-507, the disclosure of which is hereby incorporated herein by reference. The partially deleted adenoviral expression system is further described in WO99/57296, the disclosure of which is hereby incorporated by reference herein.

Adeno-associated virus (AAV) is a single-stranded human DNA parvovirus whose genome has a size of 4.6 kb. The AAV genome contains two major genes: the rep gene, which codes for the rep proteins (Rep 76, Rep 68, Rep 52, and Rep 40) and the cap gene, which codes for AAV replication, rescue, transcription and integration, while the cap proteins form the AAV viral particle. AAV derives its name from its dependence on an adenovirus or other helper virus (e.g., herpesvirus) to supply essential gene products that allow AAV to undergo a productive infection, i.e., reproduce itself in the host cell. In the absence of helper virus, AAV integrates as a provirus into the host cell's chromosome, until it is rescued by superinfection of the host cell with a helper virus, usually adenovirus (Muzyczka, Curr. Top. Micor. Immunol. 158:97-127, 1992).

Interest in AAV as a gene transfer vector results from several unique features of its biology. At both ends of the AAV genome is a nucleotide sequence known as an inverted terminal repeat (ITR), which contains the cis-acting nucleotide sequences required for virus replication, rescue, packaging and integration. The integration function of the ITR mediated by the rep protein in trans permits the AAV genome to integrate into a cellular chromosome after infection, in the absence of helper virus. This unique property of the virus has relevance to the use of AAV in gene transfer, as it allows for a integration of a recombinant AAV containing a gene of interest into the cellular genome. Therefore, stable genetic transformation, ideal for many of the goals of gene transfer, may be achieved by use of rAAV vectors. Furthermore, the site of integration for AAV is well-established and has been localized to chromosome 19 of humans (Kotin et al., Proc. Natl. Acad. Sci. 87:2211-2215, 1990). This predictability of integration site reduces the danger of random insertional events into the cellular genome that may activate or inactivate host genes or interrupt coding sequences, consequences that can limit the use of vectors whose integration of AAV, removal of this gene in the design of rAAV vectors may result in the altered integration patterns that have been observed with rAAV vectors (Ponnazhagan et al., Hum Gene Titer. 8:275-284, 1997).

There are other advantages to the use of AAV for gene transfer. The host range of AAV is broad. Moreover, unlike retroviruses, AAV can infect both quiescent and dividing cells. In addition, AAV has not been associated with human disease, obviating many of the concerns that have been raised with retrovirus-derived gene transfer vectors.

Standard approaches to the generation of recombinant rAAV vectors have required the coordination of a series of intracellular events: transfection of the host cell with an rAAV vector genome containing a transgene of interest flanked by the AAV ITR sequences, transfection of the host cell by a plasmid encoding the genes for the AAV rep and cap proteins which are required in trans, and infection of the transfected cell with a helper virus to supply the non-AAV helper functions required in trans (Muzyczka, N., Curr. Top. Micor. Immunol. 158:97-129, 1992). The adenoviral (or other helper virus) proteins activate transcription of the AAV rep gene, and the rep proteins then activate transcription of the AAV cap genes. The cap proteins then utilize the ITR sequences to package the rAAV genome into an rAAV viral particle. Therefore, the efficiency of packaging is determined, in part, by the availability of adequate amounts of the structural proteins, as well as the accessibility of any cis-acting packaging sequences required in the rAAV vector genome.

Retrovirus vectors are a common tool for gene delivery (Miller, Nature (1992) 357:455-460). The ability of retrovirus vectors to deliver an unrearranged, single copy gene into a broad range of rodent, primate and human somatic cells makes retroviral vectors well suited for transferring genes to a cell.

Retroviruses are RNA viruses wherein the viral genome is RNA. When a host cell is infected with a retrovirus, the genomic RNA is reverse transcribed into a DNA intermediate which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences enabling encapsidation without coincident production of a contaminating helper virus. A helper virus is not required for the production of the recombinant retrovirus if the sequences for encapsidation are provided by co-transfection with appropriate vectors.

The retroviral genome and the proviral DNA have three genes: the gag, the pol, and the env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication. Lentiviruses have additional genes including vit vpr, tat, rev, vpu, nef, and vpx (in HD/-1, HIV-2 and/or SIV). Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the result is a cis defect which prevents encapsidation of genomic RNA. However, the resulting mutant is still capable of directing the synthesis of all varion proteins.

Lentiviruses are complex retroviruses which, in addition to the common retroviral genes gag, pol and env, contain other genes with regulatory or structural function. The higher complexity enables the lentivirus to modulate the life cycle thereof, as in the course of latent infection. A typical lentivirus is the human immunodeficiency virus (HIV), the etiologic agent of AIDS. In vivo, HIV can infect terminally differentiated cells that rarely divide, such as lymphocytes and macrophages. In vitro, HIV can infect primary cultures of monocyte-derived macrophages (MDM) as well as HeLa-Cd4 or T lymphoid cells arrested in the cell cycle by treatment with aphidicolin or gamma irradiation. Infection of cells is dependent on the active nuclear import of HIV preintegration complexes through the nuclear pores of the target cells. That occurs by the interaction of multiple, partly redundant, molecular determinants in the complex with the nuclear import machinery of the target cell. Identified determinants include a functional nuclear localization signal (NLS) in the gag matrix (MA) protein, the karyophilic virion-associated protein, vpr, and a C-terminal phosphotyrosine residue in the gag MA protein. The use of retroviruses for gene therapy is described, for example, in U.S. Pat. No. 6,013,516; and U.S. Pat. No. 5,994,136, the disclosures of which are hereby incorporated herein by reference.

Other methods for delivery of DNA to cells do not use viruses for delivery. For example, cationic amphiphilic compounds can be used to deliver the nucleic acid of the present invention. Because compounds designed to facilitate intracellular delivery of biologically active molecules must interact with both non-polar and polar environments (in or on, for example, the plasma membrane, tissue fluids, compartments within the cell, and the biologically active molecular itself), such compounds are designed typically to contain both polar and non-polar domains. Compounds having both such domains may be termed amphiphiles, and many lipids and synthetic lipids that have been disclosed for use in facilitating such intracellular delivery (whether for in vitro or in vivo application) meet this definition. One particularly important class of such amphiphiles is the cationic amphiphiles. In general, cationic amphiphiles have polar groups that are capable of being positively charged at or around physiological pH, and this property is understood in the art to be important in defining how the amphiphiles interact with the many types of biologically active (therapeutic) molecules including, for example, negatively charged polynucleotides such as DNA.

The use of compositions comprising cationic amphiphilic compounds for gene delivery is described, for example, in U.S. Pat. Nos. 5,049,386; 5,279,833; 5,650,096; 5,747,471; 5,767,099; 5,910,487; 5,719,131; 5,840,710; 5,783,565; 5,925,628; 5,912,239; 5,942,634; 5,948,925; 6,022,874; 5,994,317; 5,861,397; 5,952,916; 5,948,767; 5,939,401; and 5,935,936, the disclosures of which are hereby incorporated herein by reference.

In addition, nucleic acid of the present invention can be delivered using "naked DNA." Methods for delivering a non-infectious, non-integrating DNA sequence encoding a desired polypeptide or peptide operably linked to a promoter, free from association with transfection-facilitating proteins, viral particles, liposomal formulations, charged lipids and calcium phosphate precipitating agents are described in U.S. Pat. Nos. 5,580,859; 5,963,622; 5,910,488; the disclosures of which are hereby incorporated herein by reference.

Gene transfer systems that combine viral and nonviral components have also been reported. Cristiano et al., (1993) Proc. Natl. Acad. Sci. USA 90:11548; Wu et al. (1994) J. Biol. Chem. 269:11542; Wagner et al. (1992) Proc. Natl. Acad. Sci. USA 89:6099; Yoshimura et al. (1993) J. Biol. Chem. 268: 2300; Curiel et al. (1991) Proc. Natl. Acad. Sci. USA 88:8850; Kupfer et al. (1994) Human Gene Ther. 5:1437; and Gottschalk et al. (1994) Gene Ther. 1:185. In most cases, adenovirus has been incorporated into the gene delivery systems to take advantage of its endosomolytic properties. The reported combinations of viral and nonviral components generally involve either covalent attachment of the adenovirus to a gene delivery complex or co-internalization of unbound adenovirus with cationic lipid: DNA complexes.

For delivery of DNA and protein to the eye, administration will typically be local. This has the advantage of limiting the amount of DNA that needs to be administered and limiting systemic side-effects. Many possible modes of delivery can be used, including, but not limited to: topical administration on the cornea by a gene gun; subconjunctival injection, intracameral injection, via eye drops to the cornea, injection into the anterior chamber via the termporal limbus, intrastromal injection, corneal application combined with electrical pulses, intracorneal injection, subretinal injection, intravitreal injection, and intraocular injection. Alternatively cells can be transfected or transduced ex vivo and delivered by intraocular implantation. See, Auricchio, Mol. Ther. 6: 490-494, 2002; Bennett, Nature Med. 2: 649-654, 1996; Borras, Experimental Eye Research 76: 643-652, 2003; Chaum, Survey of Ophthalmology 47: 449-469, 2002; Campochiaro, Expert Opinions in Biological Therapy 2: 537-544 (2002); Lai, Gene Therapy 9: 804 813, 2002; Pleyer, Progress in Retinal and Eye Research, 22: 277-293, 2003.

The effects of various proposed therapeutic agents and administrations can be tested in suitable animal models for particular diseases. For example, retinopathy of prematurity can be tested in an oxygen-induced retinopathy model in the mouse as described in Smith, Investigative Ophthalmology & Visual Science, 35: 101-111, 1994. Laser-induced choroidal neovascularization in a mouse can be used as a model for human choroidal neovascularilation (CNV) occurs in diseases such as age-related macular degeneration. Tobe, American Journal of Pathology 153: 1641-1646, 1998. Other models of CNV have been developed in primates, rats, minipigs, and rabbits. Mouse models of age-related macular degeneration have been developed in genetically-deficient mice. Mice deficient in either monocyte chemoattractant protein-1 or C-C chemokine receptor-2 develop features of age-related macular degeneration. Ambati, Nature Med. 9: 1390-1397, 2003.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

Two constructs were generated: the first, D2-9Gly-Fc, containing a polyglycine 9-mer (9Gly) linker and the second, D2-Fc, with the same sequence except the 9Gly linker (FIG. 1).

We analyzed the amino acid sequences of D2-9Gly-Fc and D2-Fc proteins using the Protein Analysis Toolbox of the sequence analysis program MacVector 6.5.1. (IBI, New Haven, Conn.). The polyglycine 9-mer linker in the D2-9Gly-Fc sequence was identified as a region with higher than average flexibility by the flexibility prediction method of Karpus and Schultz (1985) Naturwiss, 72: 212-213. No such region was detected in the D2-Fc sequence (FIG. 1).

Example 2

Figure 2:
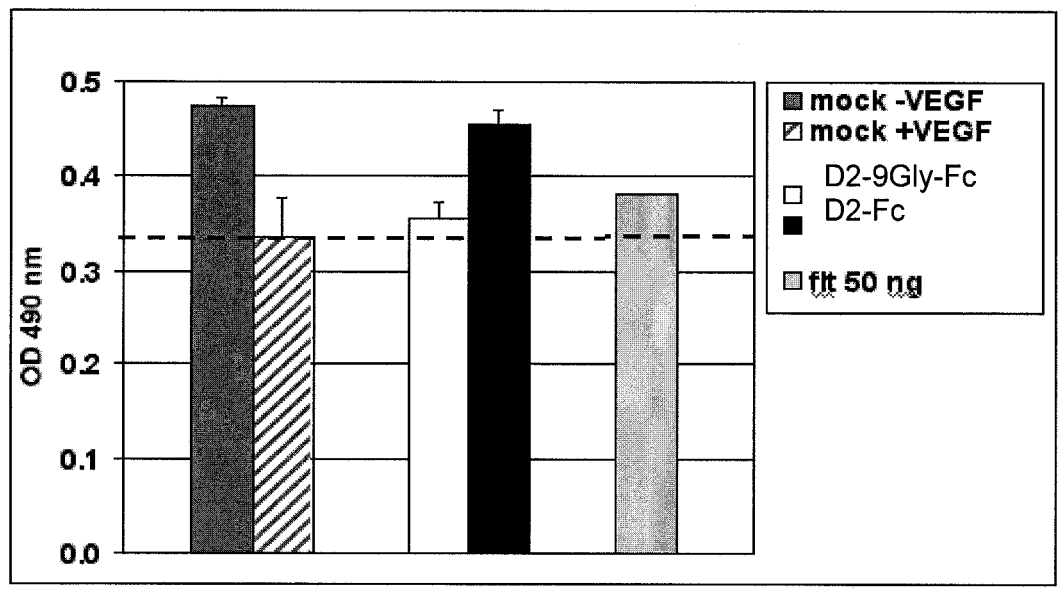
FIG. 2. Biological activity of D2-9Gly-Fc vs. D2-Fc. 293 cells were grown in the starvation media (M199+5% FCS) and transfected with plasmids containing D29Gly-Fc and D2-Fc expression cassettes under control of CMV promoter. Conditioned media (CM) was collected 72 h later. HUVECs were seeded into 96 well plate (2E3 cells/well) in starvation media+VEGF (10 ng/mL) and 50 ul CM plus VEGF (10 ng/mL) was added 24 h later. The controls (+/−VEGF) were incubated with CM from the control pEGFP (Clontech; pEGFP carries a red-shifted variant of wild-type green fluorescent protein (GFP) which has been optimized for brighter fluorescence and higher expression in mammalian cells) plasmid transfection. The positive control was treated with 50 ng of Flt-1-IgG recombinant protein (R&D Systems). The HUVECs were assayed for proliferation 3 days post treatment using CellTiter 96® AQ$_{ueous}$ reagent (Promega). The data represent the means of the average values of OD$_{490}$ of two experiments each assayed in triplicates.
Figure 3:
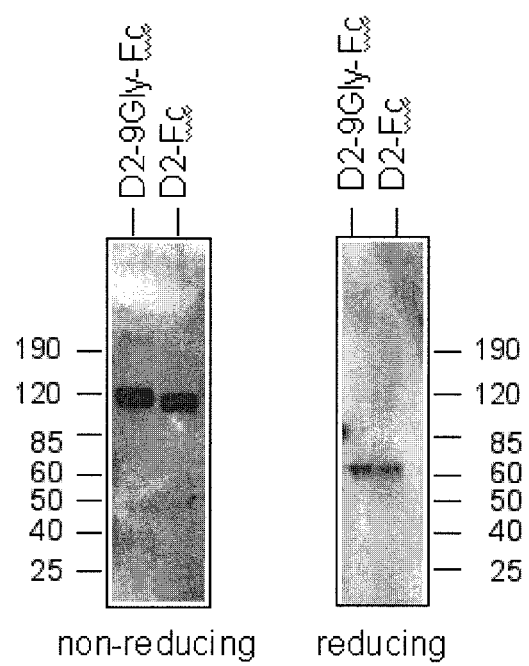
FIG. 3. Western blot analysis of D2-9Gly-Fc and D2-Fc. The size of both D2-9Gly-Fc and D2-Fc proteins appears to be twice as large while migrating in non-reducing gel as compared to migration in reducing gel. The proteins were loaded from the conditioned media following 293 cell transfection of plasmids expressing D2-9Gly-Fc and D2-Fc were separated by SDS-electrophoresis and transferred to PVDF membrane. The blot was probed with goat anti-human anti-IgG1 Fc and rabbit anti-goat IgG-HRP antibodies.

We tested an isolated Flt-1 Flt-1 Ig-like domain 2 connected to the IgG1 Fc region by a flexible polyglycine 9-mer linker (D2-9Gly-Fc). The D2-9Gly-Fc fusion protein is capable of efficiently binding VEGF and of inhibiting VEGF-dependent human umbilical vein endothelial cell (HUVEC) proliferation. See FIG. 2. In contrast, when Flt-1 Ig-like domain 2 is linked directly to the IgG1 heavy chain (Fc) to form D2-Fc, only minimal VEGF binding was observed. See FIG. 2. Both the dimerization via IgG1 Fc and the insertion of a flexible linker appear to facilitate VEGF binding to Flt-1 domain 2. The presence of dimeric forms in both D2-9Gly-Fc and D2-Fc were confirmed by the Western blot analysis. See FIG. 3.

Example 3

An intravitreal injection of AAV vector (1×108 to 1×109 particles in a volume of 0.0005 mL) is administered to newborn (P0) or 1 day old (P1) C57BL/6 mice. Retinal neovascularization (NV) is induced in C57BL/6 mice by exposing P7 pups and their nursing dam to hyperoxia for 5 days. The pups are returned to room air on P12 and are euthanized at P17 (time of peak NV). (Smith L E H, Weslowski E, McLellan A, Kostyk S K, D'Amato R, Sullivan and D'Amore P A. Oxygen-Induced Retinopathy in the Mouse. Invest Opth Vis Sci. 1994; 35:101-111.) Entire paraffin embedded eyes are serially cross sectioned at 5 micron intervals. The degree of NV is determined by counting the number of endothelial cell nuclei internal to the inner limiting membrane in sections taken every 100 microns.

Cohorts of animals treated with the AAV vectors coding for the anti-angiogenic agents are compared to cohorts treated with vectors coding for irrelevant transgenes or with vectors that do not code for a transgene. The average number of endothelial cell nuclei in each treated eye is compared to each animal's untreated fellow eye.

Example 4

Generation of D2-9Gly-Ex3/CH3

Domain 2 of Flt-1 has been shown to be essential for VEGF165 binding. However, it was demonstrated that Flt-1 domain 2 alone was incapable of binding VEGF A. (Davis-Smyth et al., 1996.) VEGF A, when present as a dimer, binds to Flt-1 through acidic residues (amino acids 63-67 of the mature protein) that allows a possible mechanism for ligand-induced dimerization of receptor (Keyt et al., 1996).

Therefore, a dimerization of domain 2 of Flt-1 was used as a strategy to restore the binding of domain 2 of Flt-1 to VEGF A. Fusion with a fragment of IgG heavy chain can be used for dimerization of proteins (Davis-Smyth et al., 1996). Here we demonstrate that amino acids 75-88 (i.e., PSCVPLMRCG-GCCN; SEQ ID NO: 13) of VEGF A (SEQ ID NO: 12) increase the biological activity of sFlt-1 hybrid proteins.

Figure 4:
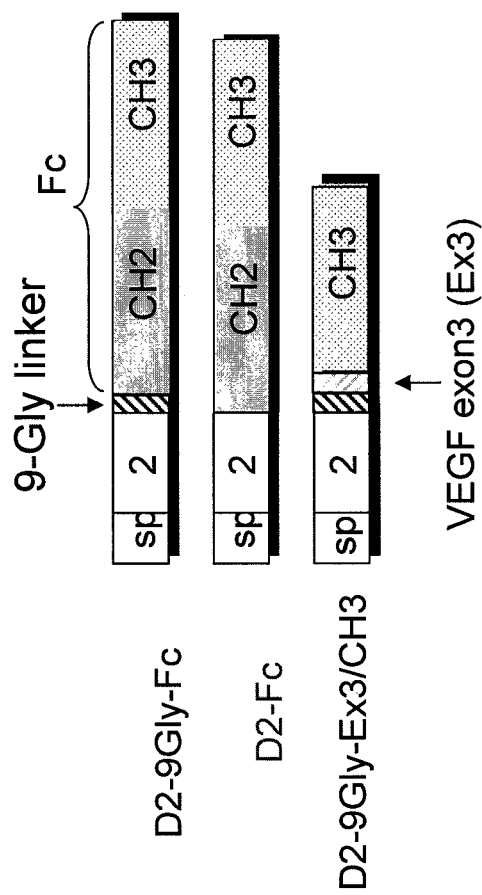
FIG. 4. sFlt-1 hybrid proteins containing 9Gly linker and VEGF Ex3. Structure comparison of D2-9Gly-Ex3/CH3 to previously constructed proteins. All three proteins contain identical amino acid sequence of Flt-1 domain 2, consisting of 24 aa of Flt-1 signal peptide and 93 aa of Flt-1 domain 2. D2-9Gly-Ex3/CH3 contains 9 aa of 9Gly linker, 14 aa of VEGF Ex3 and 120 aa of the CH3 region of human IgG1 heavy chain Fc.

Initially, three hybrid proteins were engineered: D2-9Gly-Fc, D2-Fc and D2-9GlyEx3/CH3 (FIG. 4). All three hybrid proteins contain the same Flt-1 domain D2 as D29Gly-Fc. No VEGF binding was observed with D2-Fc, which does not contain the polyglycine 9-mer (9Gly) linker. The third protein, D2-9Gly-Ex3/CH3, contains the polyglycine 9-mer (9Gly) linker and the multimerization domain of VEGF (aa PSCVPLMRCGGCCN; SEQ ID NO: 13; VEGF Ex3), but it also contains the CH3 region of human IgG1 heavy chain Fc (aa 371-477 of the SEQ ID NO: 10).

Figure 5:
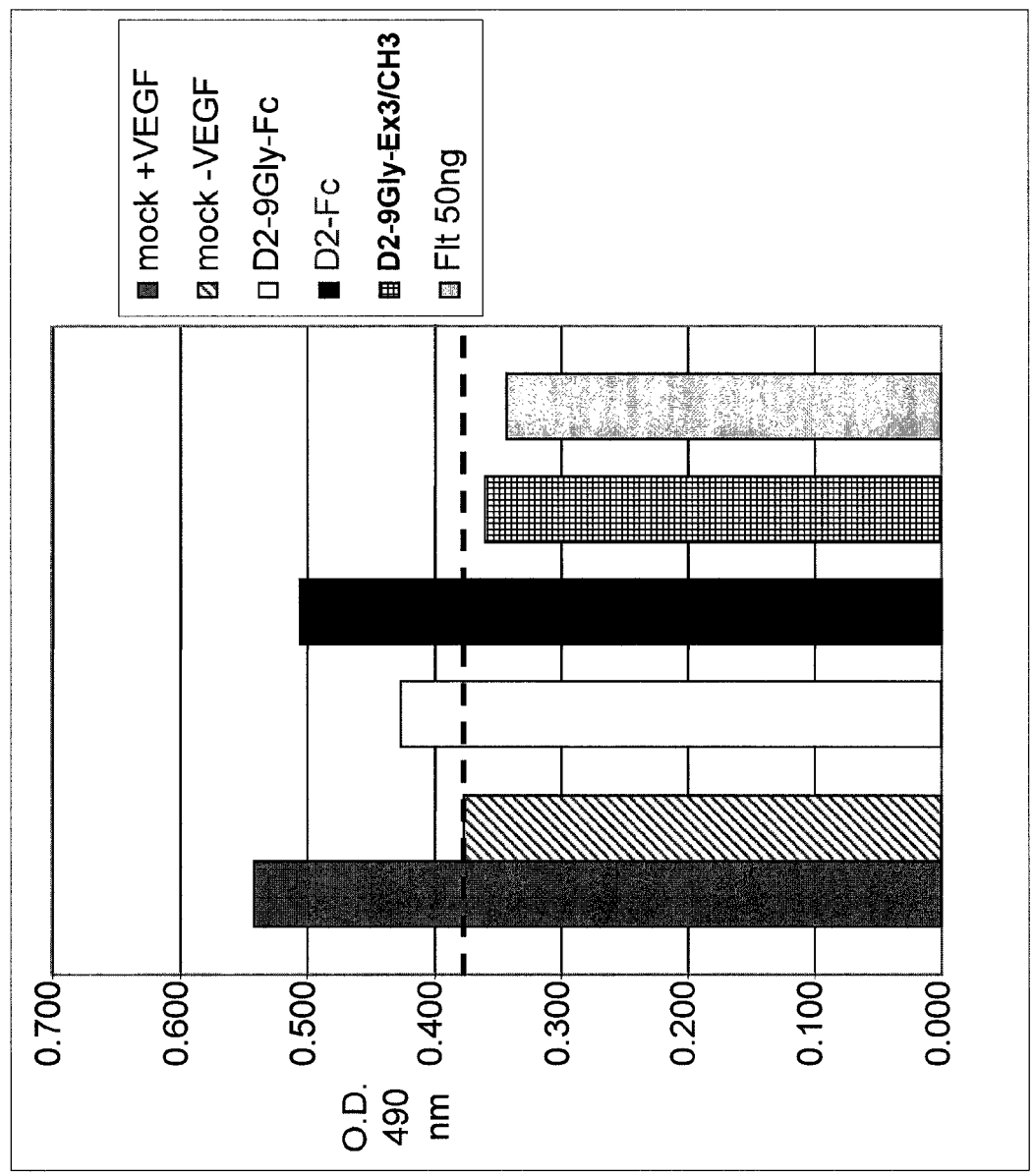
FIG. 5. Biological activity of D2-9Gly-Ex3/CH3 vs. D2-9Gly-Fc. Protein D2-9GlyEx3/CH3, where domain 2 is connected to the CH3 region through 9Gly linker and VEGF Ex 3, is also efficiently inhibiting VEGF-dependent HUVECs proliferation as compared to control proteins D2-9Gly-Fc and D2-Fc. 50 ng of the recombinant Flt-1-IgG (R&D Systems) was used as a control.

The protein D2-Fc did not show efficient inhibitory activity in the HUVEC proliferation assay (FIG. 5) and by implication did not bind to VEGF165 efficiently. However, the third hybrid protein, D2-9Giy-Ex3/CH3, which comprises domain 2 of Flt-1 fused to the CH3 region via both the 9Gly linker and the dimerization region of VEGF165 (Ex 3), did demonstrate inhibitory activity in a VEGF-dependent HUVECs proliferation assay (FIG. 5). This implies that this hybrid protein binds to VEGF165 efficiently.

Example 5

Using Linker (Gly4Ser)3 in Flt-1 D2 Construct

The use of several polyglycine linkers has been previously described for improvement of protein features (Mouz et al., 1996; Qiu et al., 1998). For the next construct we have used another type of linker, the 15-mer (Gly-Gly-Gly-Gly-Ser)3 (Huston et al., 1988). D2-(Gly4Ser)3-Fc protein was generated and it contains Flt-1 domain 2, (Gly4Ser)3 linker and the Fe region of human IgG1 heavy chain.

Figure 6:
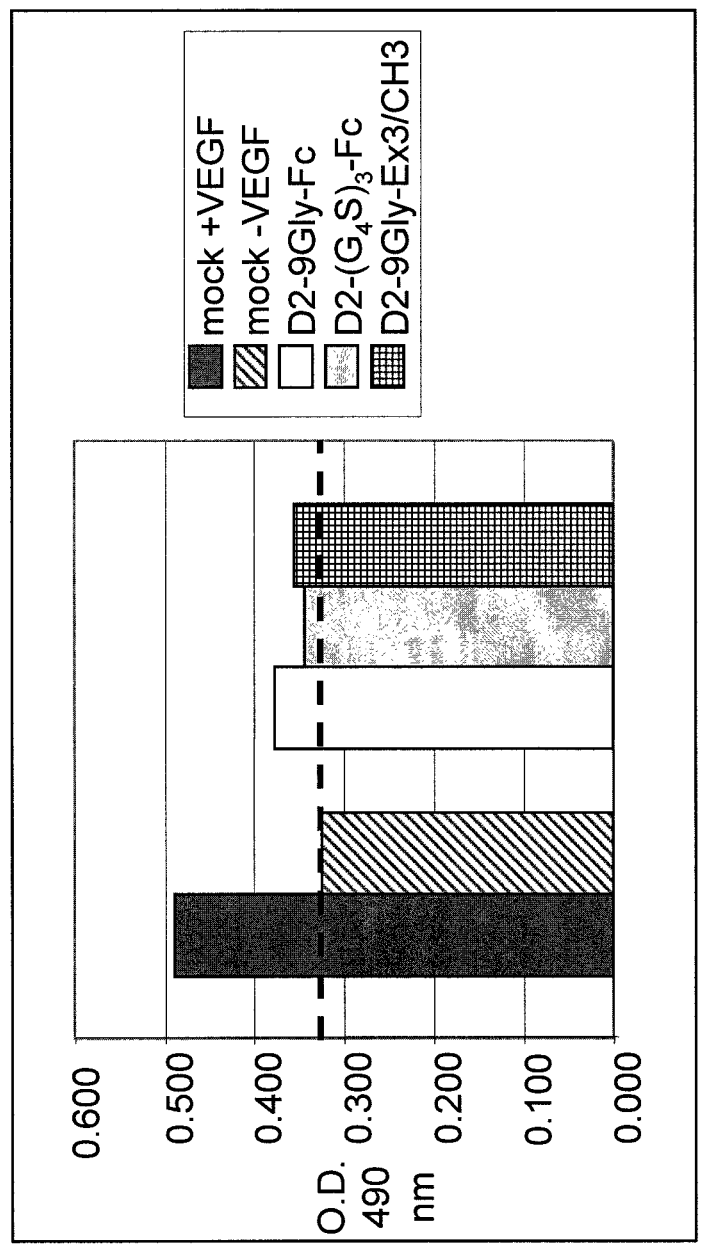
FIG. 6. HUVECs proliferation assay comparing D2-(Gly$_4$Ser)$_3$-Fc protein activity with D2-9Gly-Fc and D2-9Gly-Ex3/CH3.
Figure 7:
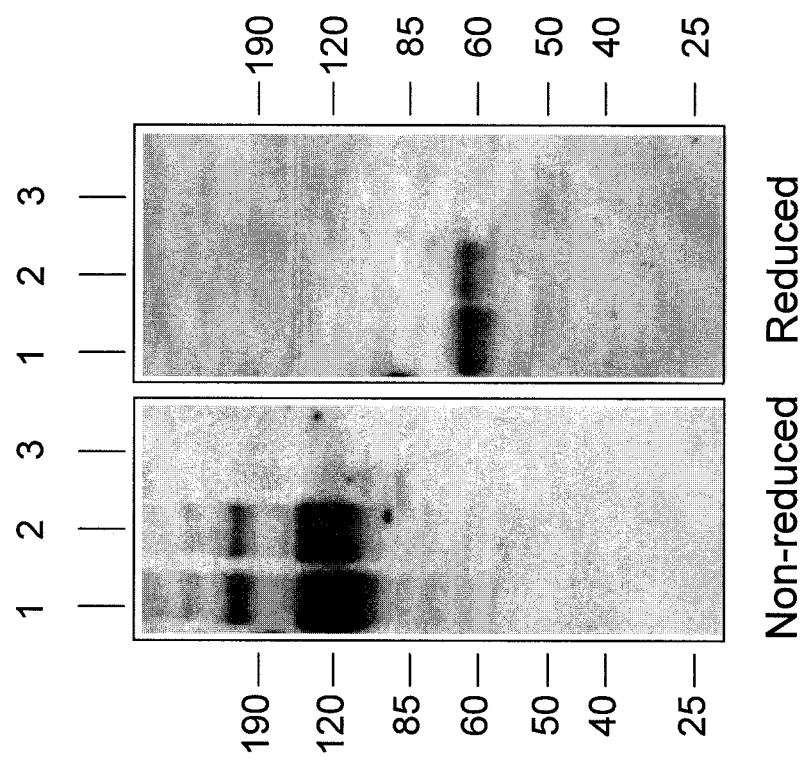
FIG. 7. Western blot. Proteins (non-reduced and reduced) from conditioned medium of transfected 293 cells (15 ul of CM) with plasmids expressing (1): D2-9Gly-Fc; (2): D2-(G4S)$_3$-Fc and (3) -EGFP proteins were separated by SDS-electrophoresis and transferred to PVDF membrane. The blot was probed with goat anti-human IgG1 Fc and rabbit anti-goat IgG-HRP antibodies.

D2-(Gly4Ser)3-Fc was further characterized in HUVECs proliferation assay. Biological activity of D2-(Gly4Ser)3-Fc as measured by inhibition of HUVEC proliferation was similar to that of D2-9Gly-Fc and D2-9Gly-Ex3/CH3 (FIG. 6).

Figure 9:
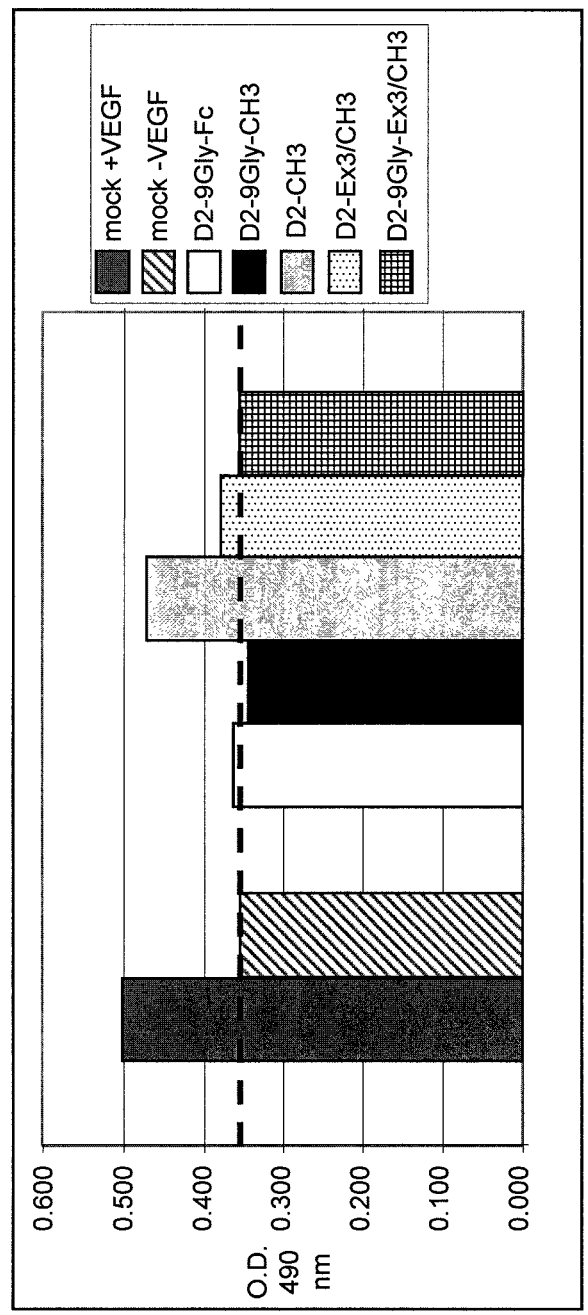
FIG. 9. HUVECs proliferation assay with the Flt-1(D2) constructs with 9Gly, Ex3 and CH3 combinations. Conditioned media from 293 cells (5 ul) containing proteins D2-Ex3/CH3, D2-9Gly-CH3 and D2-CH3 were compared to D2-9Gly-Fc and D2-9Gly-Ex3/CH3.

The D2-(Gly4Ser)3-Fc construct was further characterized by Western blot and compared to D2-9Gly-Fc (FIG. 9). Both constructs are present mostly in a dimer form and the monomer forms were detected after separation of reduced samples.

Example 6

Role of 9Gly or VEGF Ex3 in Flt-1 (D2) Constructs

Figure 8:
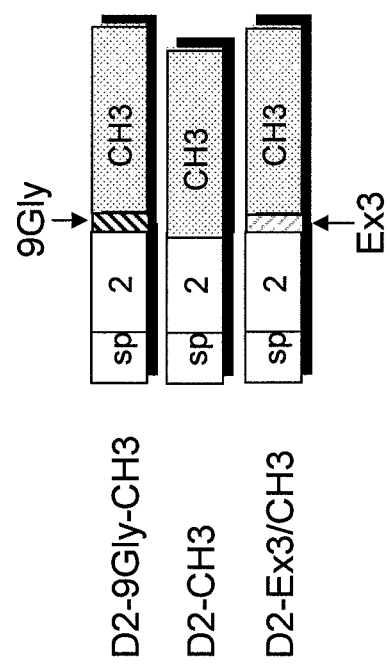
FIG. 8. Combinations of proteins with/without 9Gly linker or VEGF Ex3. Structure comparison of three novel proteins with or without 9Gly linker and/or VEGF Ex3, D2-9Gly-CH3, D2-CH3 and D2-Ex3/CH3.

In order to investigate the role of 9Gly linker or VEGF dimerizing sequence Ex3 on soluble receptor VEGF binding, three other constructs were generated: D2-9Gly-CH3, D2-CH3 and D2-Ex3/CH3 (FIG. 8). All three constructs were generated and like all the previous constructs were also put under control of CMV promoter. Their VEGF blocking activity was assessed in HUVECs proliferation assay (FIG. 9).

The HUVEC proliferation assay of proteins containg the CH3 region of IgG1 has shown that D2-9Gly-CH3 (without Ex3) and protein D2-Ex3/CH3 (without 9Gly linker) had similar VEGF blocking potency as compared to the parental D2-9GlyEx3/CH3 protein. However, protein D2-CH3 appeared to be the weakest VEGF inhibitor from all of them (FIG. 9).

Figure 10:
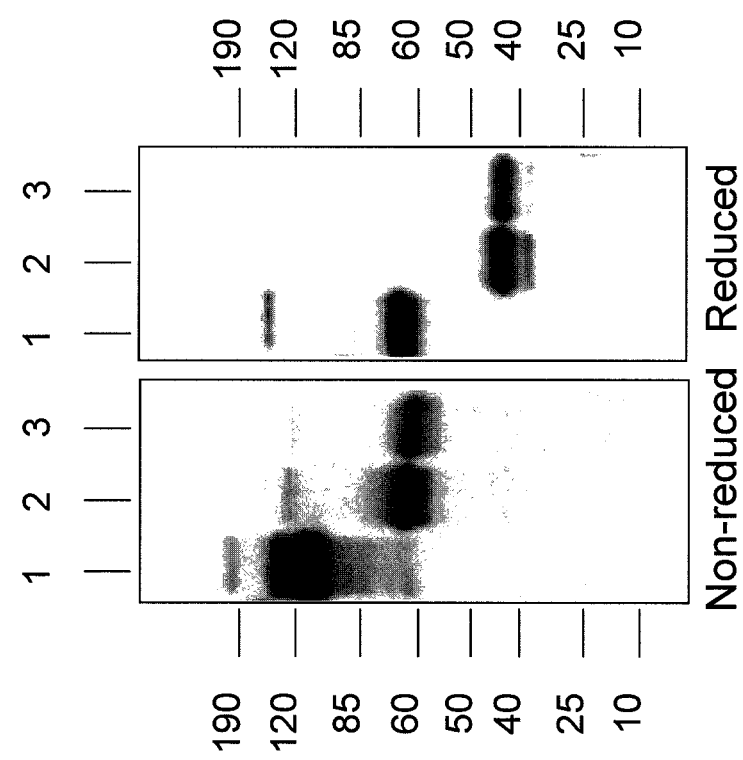
FIG. 10 Western blot. 293 cells were transfected with plasmids expressing: (1) D2-9Gly-Fc; (2) D2-9Gly-CH3 (52/26 kDa); and (3) D2-CH3 (50/25 kDa). Proteins from 293 cells conditioned medium (15 ul of CM non-reduced and/or reduced) were separated by SDS-electrophoresis and transferred to PVDF membrane. The blot was probed with anti-human VEGF-R1 HRP conjugate (R&D Systems).

The Flt-1 ELISA data of conditioned media from transfected 293 cells has shown similar Flt-1 levels for D2-9Gly-Ex3/CH3, D2-9Gly-CH3 and D2-Ex3/CH3 and D2CH3 (70-90 ng/ml) and a little higher (~150 ng/ml) for the least active form of D2CH3. Western blot of D2-9Gly-CH3 and D2-CH3 constructs (FIG. 10) is showing a prevalence of dimer forms in non-reduced conditions.

Example 7

D2-9Gly-Fc Binds VEGF Better than all Constructs

VEGF binding assay allows us to compare the relative VEGF binding affinities of our soluble VEGF receptors in a cell free system.

Figure 11:
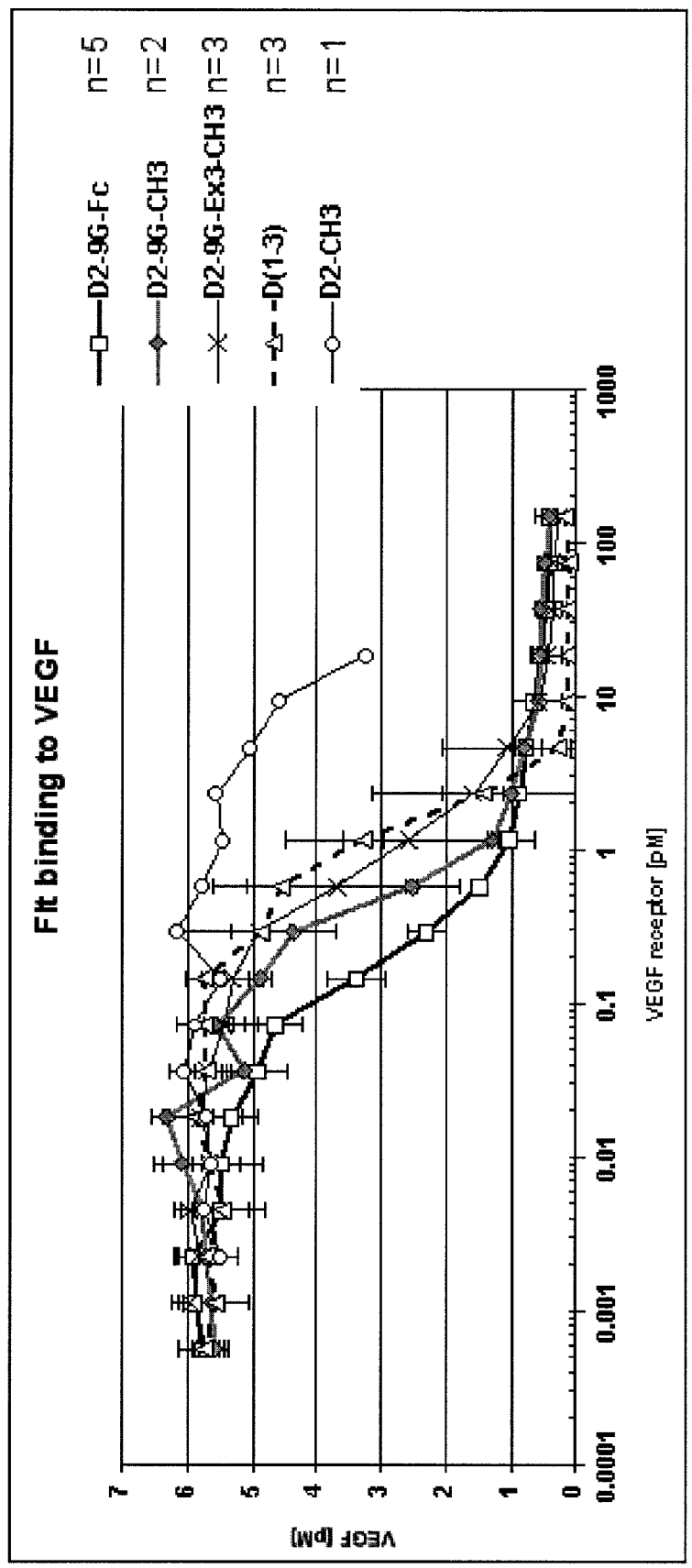
FIG. 11. VEGF "in vitro" binding assay. Conditioned media from 293 cells containing known concentrations of both D2-9Gly-Fc and Flt-1 D(1-3) control soluble receptors (ranging in concentrations from 0.29-150 µM) were serially diluted and mixed with 10 µM VEGF. The amount of unbound VEGF was then measured by ELISA. D2-9Gly-Fc binds VEGF with higher affinity than all other constructs. "n" represents the number of independent experiments (transfection and binding assay).
Figure 12:
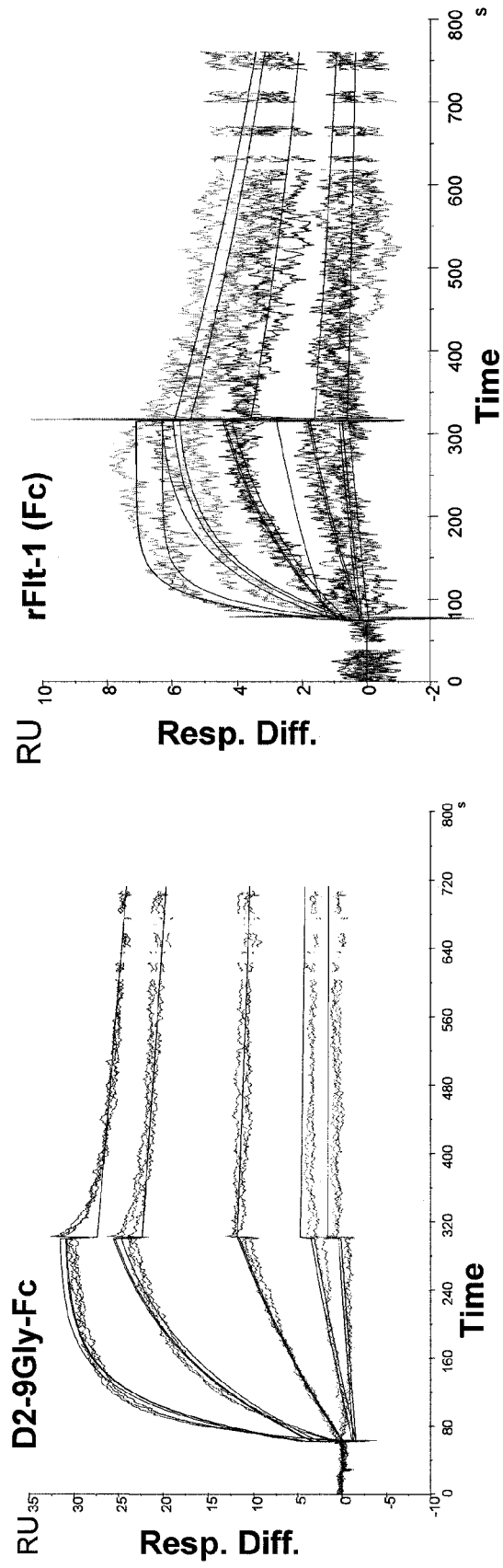
FIG. 12. The binding kinetics of the soluble Flt-1 constructs were measured by surface plasmon resonance with a BIAcore instrument. sFlt-1 constructs were immobilized onto a sensor chip, and VEGF165 was injected at concentrations ranging from 0.2 to 15 nM. The sensorgrams were evaluated using the BIA Evaluation program, the rate constants Ka and Kd were determined and the dissociation constant (KD) calculated from the ratio of Kd/Ka=KD. The lower KD value means better affinity.
Figure 14:
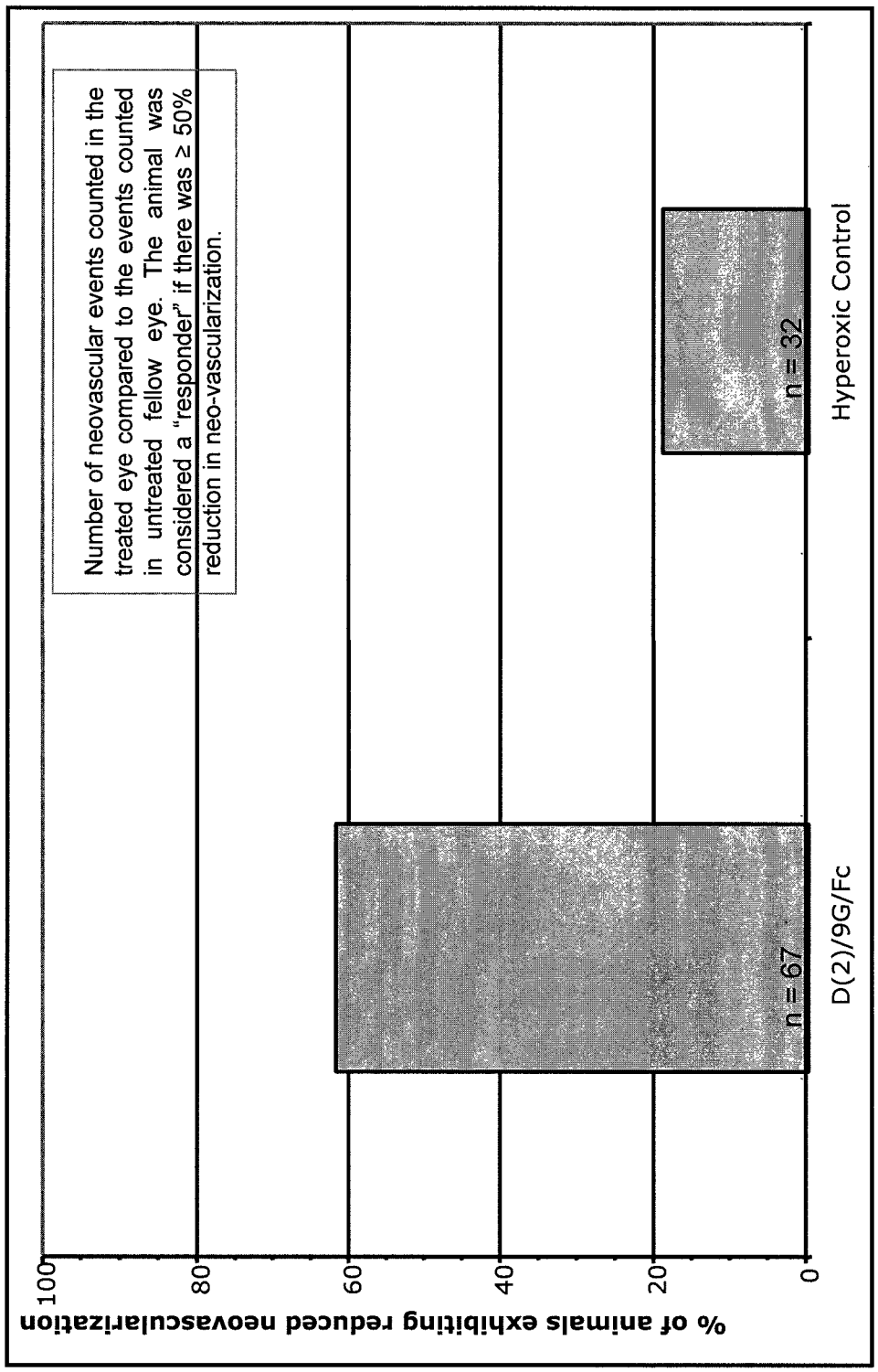
FIG. 14. Using a murine oxygen-induced retinopathy (OIR) model of retinal neovascularization (NV), one of the Flt-1 constructs was administered to the mouse eyes and neovascularization was determined. The mice were exposed to hyperoxic conditions. The number of neovascular events was determined in the treated eyes compared to the events in the untreated eyes of the same animals. The animal was considered a "responder" if there was a greater than 50% reduction in neovascular events.

Briefly, conditioned media containing known concentrations of soluble receptor (ranging in concentrations from 0.29-150 pM) were serially diluted and mixed with 10 pM VEGF. The amount of unbound VEGF was then measured by ELISA. D2-9Gly-Fc binds VEGF with higher affinity to bind VEGF at receptor concentrations from 0.001 to ~0.2 pM than all other constructs. D2-CH3 has the lowest affinity to bind VEGF (FIG. 11).

References

Davis-Smyth, et al., EMBO J., 15, 1996, 4919
Huston, J. S., et al. (1991) Methods Enzymol. 203, 46-88
Huston, J. S., et al. (1988) Proc. Natl. Acad. Sci. USA, 85, 5879-5883.
Johnson, S., et al. (1991) Methods Enzymol. 203, 88-98 Karpus, P. A., et al. (1985)
Naturwiss., 72, 212-213.
Keyt, B. A., et al. (1996) J. Biol. Chem. 271: 5638-5646.
Kortt, A. A., et al. (1997)
Protein Engng, 10, 423-433. Lee, Y-L., et al. (1998) Human Gene Therapy, 9, 457-465

Mouz N., et al. (1996) Proc. Nati Acad. Sci. USA, 93, 9414-9419.

Nielsen, et al. (1997) Protein Eng., 10, 1

Qiu, H., et al. (1998) J. Biol. Chem. 273: 11173-11176.

Table of Sequences

| SEQ ID NO | Clone Name | Length | Type |
|---|---|---|---|
| 1 | FLT1D29GLYFC | 1077 | DNA |
| 2 | FLT1D29GLYFC | 358 | Protein |
| 3 | FLT1D2DEL9GLY | 1050 | DNA |
| 4 | FLT1D2DEL9GLY | 349 | Protein |
| 5 | FLT1D29GLYVEG | 426 | DNA |
| 6 | FLT1D29GLYVEG | 141 | Protein |
| 7 | FLT1D29GLYVEG | 744 | DNA |
| 8 | FLT1D29GLYVEG | 247 | Protein |
| 9 | iGg1 HEAVY | 1434 | DNA |
| 10 | IgG1 HEAVY | 477 | Protein |
| 11 | VEGF | 648 | DNA |
| 12 | VEGF | 215 | Protein |
| 13 | VEGF exon 3 | 14 | Protein |
| 14 | FLT-1 | 5777 | DNA |
| 15 | FLT-1 | 1338 | Protein |

Table of Sequences

| SEQ ID NO | Clone Name | Length | Type |
|---|---|---|---|
| 16 | KDR | 5830 | DNA |
| 17 | KDR | 1356 | Protein |
| 18 | D2-CH3 | 675 | DNA |
| 19 | D2-CH3 | 224 | Protein |
| 20 | D2-EX3-CH3 | 717 | DNA |
| 21 | D2-EX3-CH3 | 238 | Protein |
| 22 | D2-9GLY-CH3 | 702 | DNA |
| 23 | D2-9GLY-CH3 | 233 | Protein |
| 24 | D2(G4S)3-Fc | 1095 | DNA |
| 25 | D2(G4S)3-FC | 364 | Protein |
| 26 | random linker | 9 | Protein |
| 27 | linker | 9 | Protein |
| 28 | linker | 9 | Protein |
| 29 | linker | 9 | Protein |
| 30 | linker | 9 | Protein |
| 31 | linker | 15 | Protein |
| 32 | linker | 13 | Protein |
| 33 | linker | 9 | Protein |
| 34 | linker | 23 | Protein |

We claim:

1. A fusion protein of the formula X-Y-Z, wherein
X comprises the Ig-like domain 2 of VEGF-R1 but lacks the Ig-like domains 1 and 3 of a VEGF receptor, with said Ig-like domain 2 of VEGF-R1 being covalently linked to moiety Z via moiety Y; and
Y is selected from the group consisting of gly$_9$ (SEQ ID NO: 27), glu$_9$ (SEQ ID NO: 28), ser$_9$ (SEQ ID NO: 29), gly$_5$-cys -pro$_2$-cys (SEQ ID NO: 30), (gly$_4$ser)$_3$ (SEQ ID NO: 31), Ser-Cys-Val-Pro-Leu-Met-Arg-Cys -Gly-Gly-Cys-Cys-Asn (SEQ ID NO: 32), Pro-Ser-Cys-Val-Pro-Leu-Met-Arg-Cys- Gly-Gly -Cys-Cys-Asn (SEQ ID NO: 13), Gly-Asp-Leu-Ile-Tyr-Arg-Asn-Gln-Lys (SEQ ID NO: 26), and Gly$_9$-Pro-Ser-Cys-Val-Pro-Leu-Met-Arg-Cys-Gly-Gly-Cys-Cys-Asn (SEQ ID NO: 34), and
Z is a CH3 region of an IgG heavy chain molecule or an Fc portion of an antibody molecule.

2. The fusion protein of claim 1, wherein X consists of the IgG-like domain 2 of VEGF-R1 (FLT-1).

3. The fusion protein of claim 1, wherein said fusion protein is capable of binding to VEGF.

4. The fusion protein of claim 1, wherein Z is an IgG1 CH3 region.

5. The fusion protein of claim 1, wherein Z is an IgG2 CH3 region.

6. The fusion protein of claim 1, wherein the Fc is an IgG Fc.

7. The fusion protein of claim 6, wherein the IgG Fc is IgG1 Fc.

8. A composition comprising the fusion protein of claim 1 which further, comprises one or more pharmaceutically acceptable excipients or carriers.

9. The composition of claim 8, wherein said composition is a liquid formulation.

10. The composition of claim 8, wherein said composition is a lyophilized formulation.

11. A composition comprising one or more fusion proteins of claim 1, wherein said composition comprises multimers of said fusion proteins.

12. The composition of claim 11, wherein said composition comprises a single species of fusion protein which forms homomultimers.

13. The composition of claim 11, wherein said composition comprises fusion proteins, wherein the X moiety in said fusion proteins in the composition are heterogeneous.

14. The composition of claim 11, which further comprises one or more pharmaceutically acceptable excipients or carriers.

15. The composition of claim 14, wherein said composition is a liquid formulation.

16. The composition of claim 14, wherein said composition is a lyophilized formulation.

17. A nucleic acid molecule which encodes a fusion protein according to claim 1.

18. The nucleic acid molecule of claim 17, wherein Z is an Fc portion of an antibody molecule.

19. The nucleic acid molecule of claim 17, wherein X consists of the Ig-like domain 2 of VEGF-R1 (Flt-1).

20. An isolated mammalian cell which comprises the nucleic acid of claim 17.

21. The mammalian cell of claim 20 which is a human cell.

22. The mammalian cell of claim 21 which is selected from the group consisting of a fibroblast, a hepatocyte, an endothelial cell, a keratinocyte, a hematopoietic cell, synoviocyte, epithelial cell, retinal cell, and a stem cell.

23. An in vitro method for producing a transformed mammalian cell comprising delivering the nucleic acid of claim 17 to an isolated mammalian cell to form a cell which expresses said fusion protein.

24. The method of claim 23, wherein the fusion protein comprises a sequence selected from the group consisting of SEQ ID NO: 2, 8, 21, 23, and 25.

25. A method of multimerizing a polypeptide X comprising:
linking a polypeptide X to a polypeptide Z via a polypeptide Y to form polypeptide XYZ, wherein:
X comprises the Ig-like domain 2 of a VEGF receptor but lacks the Ig-like domains 1 and 3 of VEGF-R1, with said Ig-like domain 2 of VEGF-R1 being covalently liked to polypeptide Z via polypeptide Y;
Y is selected from the group consisting of gly$_9$ (SEQ ID NO: 27), glu$_9$ (SEQ ID NO: 28), ser$_9$ (SEQ ID NO: 29), gly$_5$-cys -pro$_2$-cys (SEQ ID NO: 30), (gly$_4$ser)$_3$ (SEQ ID NO: 31), Ser-Cys-Val-Pro-Leu-Met-Arg-Cys -Gly-Gly-Cys-Cys-Asn (SEQ ID NO: 32), Pro-Ser-Cys-Val-Pro-Leu-Met-Arg-Cys- Gly-Gly -Cys-Cys-Asn (SEQ ID NO: 13), Gly-Asp-Leu-Ile-Tyr-Arg-Asn-Gln-Lys (SEQ ID NO: 26), and Gly$_9$-Pro-Ser-Cys-Val-Pro-Leu-Met-Arg-Cys-Gly-Gly-Cys-Cys-Asn (SEQ ID NO: 34), and Z is a CH3 region of an IgG heavy chain molecule or an Fc portion of an antibody molecule;
whereby polypeptide XYZ multimerizes.

26. The method of claim 25, wherein polypeptide XYZ is capable of binding to VEGF.

27. The method of claim 25, wherein the step of linking comprises constructing a nucleic acid molecule which encodes each of X, Y, and Z as a single open reading frame, wherein said polypeptide XYZ is expressed from the nucleic acid construct in a host cell.

28. The method of claim 25, wherein X consists of the Ig-like domain 2 of VEGF-R1 (Flt-1).

* * * * *